US012766089B2

(12) United States Patent
Mahon et al.

(10) Patent No.: US 12,766,089 B2
(45) Date of Patent: Oct. 20, 2026

(54) CHEMICALLY CROSS-LINKED ELASTOMERS FORMED BY MICHAEL ADDITION AND COMPOSITIONS COMPRISING SUCH ELASTOMERS

(71) Applicant: NANOMETICS LLC, La Jolla, CA (US)

(72) Inventors: Andrew Bernard Mahon, San Francisco, CA (US); Michael Joseph Isaacman, New York, NY (US); Steven Isaacman, Oak Beach, NY (US)

(73) Assignee: NANOMETICS LLC, La Jolla, CA (US)

( * ) Notice: Subject to any disclaimer, the term of this patent is extended or adjusted under 35 U.S.C. 154(b) by 797 days.

(21) Appl. No.: 18/000,422

(22) PCT Filed: Jun. 18, 2021

(86) PCT No.: PCT/US2021/037992

§ 371 (c)(1),
(2) Date: Dec. 1, 2022

(87) PCT Pub. No.: WO2021/257937

PCT Pub. Date: Dec. 23, 2021

(65) Prior Publication Data

US 2023/0248635 A1 Aug. 10, 2023

Related U.S. Application Data

(60) Provisional application No. 63/040,571, filed on Jun. 18, 2020.

(51) Int. Cl.

| | |
|---|---|
| ***A61K 8/87*** | (2006.01) |
| ***A61G 19/00*** | (2006.01) |
| ***A61K 8/04*** | (2006.01) |
| ***C08G 71/04*** | (2006.01) |

(52) U.S. Cl.

CPC ................ *A61K 8/87* (2013.01); *A61G 19/00* (2013.01); *A61K 8/042* (2013.01); *C08G 71/04* (2013.01)

(58) Field of Classification Search

CPC ...................................................... A61K 8/042

See application file for complete search history.

(56) References Cited

U.S. PATENT DOCUMENTS

| | | | |
|---|---|---|---|
| 6,887,517 | B1 | 5/2005 | Cook et al. |
| 7,431,789 | B2 | 10/2008 | Mack et al. |
| 9,752,067 | B2 | 9/2017 | Pritschins et al. |
| 2013/0149318 | A1 | 6/2013 | Reynolds et al. |

FOREIGN PATENT DOCUMENTS

| | | | | |
|---|---|---|---|---|
| WO | WO2003/076537 | * | 8/2003 | ................ C08J 7/04 |
| WO | 03/076537 | A1 | 9/2003 | |
| WO | 2019/099525 | A1 | 5/2019 | |

OTHER PUBLICATIONS

Genest et al., Prog. Polymer Sci. (2017) pp. 61-110.*
Kasetaite et al., Polymers (2018) vol. 10(439) pp. 1-13.*
Ecochard et al., "Linseed oil-based thermosets by aza-Michael polymerization," Eur J Lipid Sci Technol. 122(1):1900145 (2019).
Frias et al., "Preparation of fully biobased epoxy resins from soybean oil based amine hardeners," Ind Crops Prod. 109:434-444 (2017).
International Search Report issued in International Application No. PCT/US2021/037992, mailed Nov. 15, 2021.
Genest et al., "The aza-Michael Reaction as an Alternative Strategy to Generate Advanced silicon-based (macro) Molecules and Materials," Progress in Polymer Science 72:61-110 (2017).
Kasetaite et al., "Effect of Selected Thiols on Cross-linking of Acrylated Epoxidized Soybean Oil and Properties of Resulting Polymers," Polymers 10(4):439 (2018).
Wu et al., "2A2 + BB'B" Approach to Hyperbranched Poly(amino ester)s," Macromolecules 38:5519-5525 (2005).

* cited by examiner

*Primary Examiner* — Paul V Ward
(74) *Attorney, Agent, or Firm* — MEDLER FERRO WOODHOUSE & MILLS PLLC

(57) ABSTRACT

Gel compositions containing a Michael addition elastomer formed from the reaction of a reactant molecule containing two or more Michael acceptor groups and a molecule containing one or Michael donor group with two or more active hydrogens in its molecule and capable of forming 1,4-addition products with the Michael acceptor reactants, in a topically acceptable carrier fluid. The gelled compositions may further contain a personal or healthcare active. The actives may be incorporated into the gel via either a pre or post load method.

17 Claims, 10 Drawing Sheets

CHEMICALLY CROSS-LINKED ELASTOMERS FORMED BY MICHAEL ADDITION AND COMPOSITIONS COMPRISING SUCH ELASTOMERS

TECHNICAL FIELD

This invention relates to cross-linked elastomers from the reaction of a molecule comprising two or more Michael acceptor groups and a molecule comprising a single primary amine functional group to form 1,4-additon products, and gel compositions thereof. This invention also relates to gel compositions containing a chemically cross-linked elastomer formed from the reaction of a molecule comprising two or more Michael acceptor groups and a molecule comprising two or more Michael donor groups capable of reacting with the Michael acceptor groups to form 1,4-additon products. A catalyst may be optionally used to increase the rate of formation of the Michael addition elastomer. The gel compositions may contain a personal or healthcare active. The actives may be incorporated into the gel via either a pre or post load method. Gel compositions may be further used as components in personal care, over-the-counter drug, or pharmaceutical compositions.

BACKGROUND

Silicone elastomers have been used extensively in personal care applications for their thickening and gelling efficiency, and unique silky and powdery sensory profile. Silicone elastomers are compatible with silicone-based fluids, however, silicone-based fluids for topical use are being phased out of the personal care industry due to health and environmental concerns. There is a need to develop alternatives to silicone elastomers which demonstrate efficient thickening and gelling capabilities with topically acceptable solvents (e.g., esters, triglycerides, and hydrocarbons) while imparting a favorable skin feel. Michael addition elastomers and gel compositions described herein can potentially provide desirable alternatives to silicone elastomers.

SUMMARY

This disclosure relates to a chemically cross-linked elastomer and gel compositions of a chemically cross-linked elastomer formed by conjugate addition of a first reactant comprising one or more molecules, wherein each of the one or more molecules comprises two or more Michael acceptor functional groups, with a second reactant comprising one or more molecules, wherein each of the one or more molecules comprises one primary amine or a carbon bonded to two Michael donor hydrogen atoms. The primary amine, which contains two Michael donor hydrogen atoms, or the carbon bonded to two Michael donor hydrogen atoms, can react with two Michael acceptor functional groups.

The disclosure also relates to gel compositions comprising a Michael addition elastomer prepared from the reaction of:

A) a first reactant comprising one or more molecules, wherein each of the one or more molecules comprises two or more Michael acceptor functional groups and optionally contains an OH, SH or NH functional group at a vicinal position to each of the Michael acceptor functional groups;

B) a second reactant comprising one or more molecules, wherein each of the one or more molecules comprises a Michael donor functional group with two or more Michael active hydrogen atoms to provide two or more nucleophilic reaction sites, such that the Michael donor functional group is capable of reacting with two Michael acceptor functional groups to form a 1,4-addition product, such as an amine, malonate, or both;

C) an optional reaction catalyst;

D) a topically acceptable carrier fluid.

A personal care or healthcare active (E) may be incorporated into the cross-linked elastomer gel by dissolving it in the topically acceptable solvent during the formation of the elastomer gel (pre-load method) or admixing it with a formed elastomer gel (post-load method).

The invention is further directed to the following:

A gel composition comprising an elastomer prepared by Michael addition reaction from:

A) a first reactant comprising one or more molecules, wherein each of the one or more molecules comprises two or more Michael acceptor functional groups;

B) a second reactant comprising one or more molecules, wherein each of the one or more molecules comprises one or more Michael donor functional groups, wherein each Michael donor functional group comprises two or more Michael active hydrogen atoms;

C) an optional reaction catalyst; and

D) a topically acceptable carrier fluid, at a concentration of 0% (w/w) to 99.9% (w/w) of the gel composition, preferably 20% (w/w) to 99.9% (w/w) of the gel composition.

Figure 10:
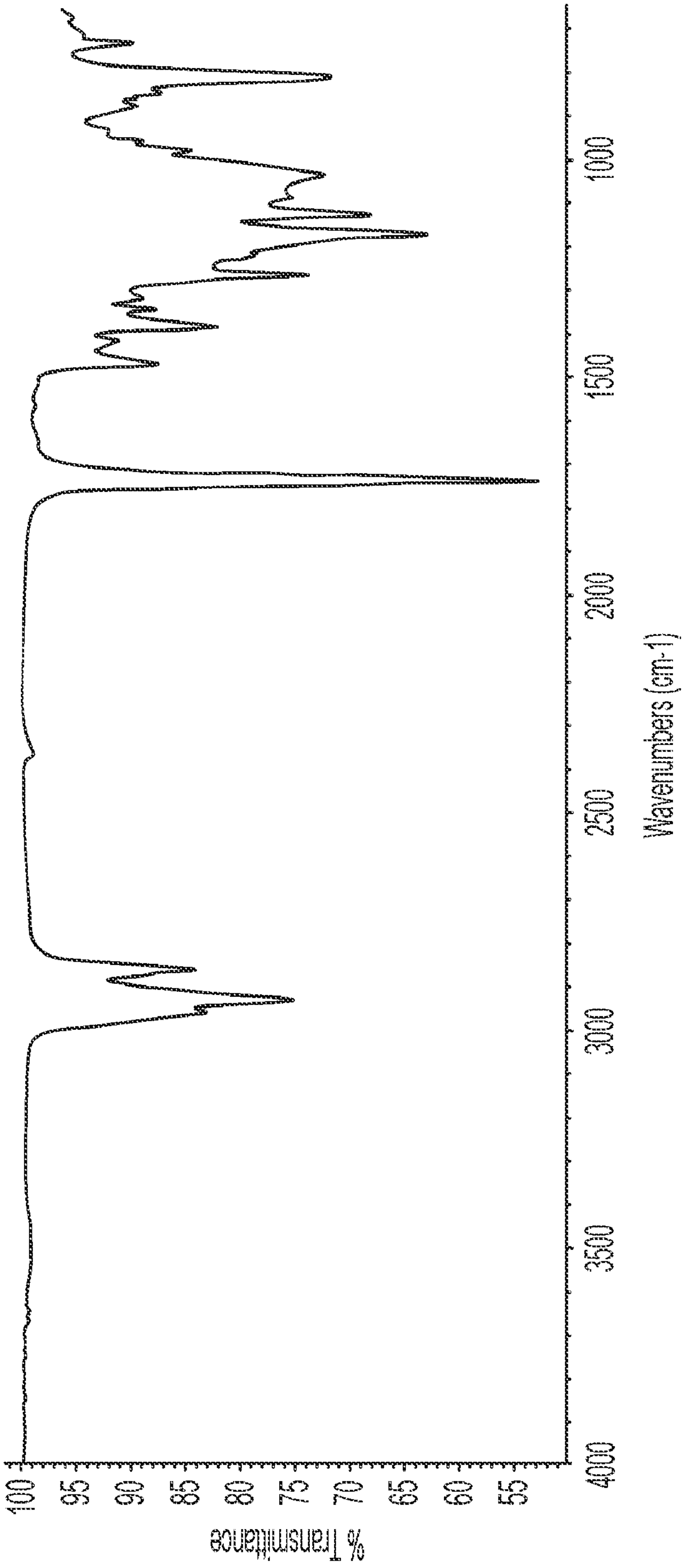

FIG. 10 shows an exemplary FTIR spectrograph of acrylated epoxidized soybean oil/poly(dimethylsiloxane), bis(3-aminopropyl) terminated aza-Michael elastomer with an acrylate/primary amine functional group ratio of 1:0.5, as described in embodiments herein.

DETAILED DESCRIPTION

This disclosure relates to a gel composition comprising a "Michael addition elastomer," which is a polymer with elastomeric properties that is chemically cross-linked by 1,4-addition products formed from the reaction between low molecular weight molecules comprising Michael acceptor functional groups and low molecular weight molecules comprising Michael donor functional groups, requiring no purification, and formed in a topically acceptable solvent from the reaction of:

A Molecule Comprising a Michael Acceptor Functional Group, (A)

In some embodiments, a first reactant for making the Michael addition elastomer described herein comprises one or more molecules comprising a Michael acceptor functional group, wherein the Michael acceptor functional group comprises two or more electrophilic reaction sites capable of reacting with a Michael donor functional group to form 1,4-addition products.

As used herein, a "Michael acceptor" is a functional group having the structure (I): $R^1R^2C{=}CR^3{-}C(O){-}$, where $R^1$, $R^2$, and $R^3$ are, independently, hydrogen or organic radicals such as for example, alkyl (linear, branched, or cyclic), aryl, alkaryl, including derivatives and substituted versions thereof. $R^1$, $R^2$, and $R^3$ may or may not, independently, contain ether linkages, carboxyl groups, further carbonyl groups, mercapto groups (also called thiol groups) or analogs thereof, nitrogen containing groups such as amines, hydroxyl groups, or combinations thereof. In one aspect, Component (A) includes one or more siloxane functional groups in its molecular or polymeric structure e.g., in the polymer backbone. In one aspect, Component (A) comprises two or more Michael acceptor functional groups. In a further aspect, Component (A) comprises an OH, SH, or NH functional group at a vicinal position to each of the Michael acceptor functional groups.

One preferred example of Component (A) is based on soybean oil, linseed oil, or other vegetable oils and has the following representative structure:

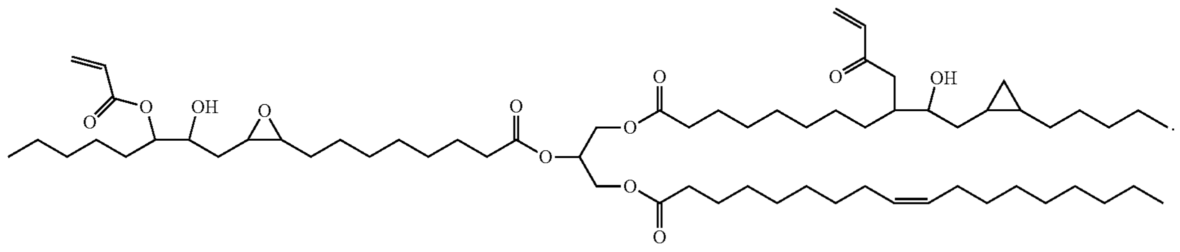 [SMILES: C=CC(=O)CC(CCCCCCCC(=O)OCC(COC(=O)CCCCCCC/C=C\CCCCCCCC)OC(=O)CCCCCCCC1OC1CC(O)C(CCCCC)OC(=O)C=C)C(O)CC1CC1CCCCC]

A further preferred example of Component (A) is based on soybean oil, linseed oil, or other vegetable oils and has the following representative structure:

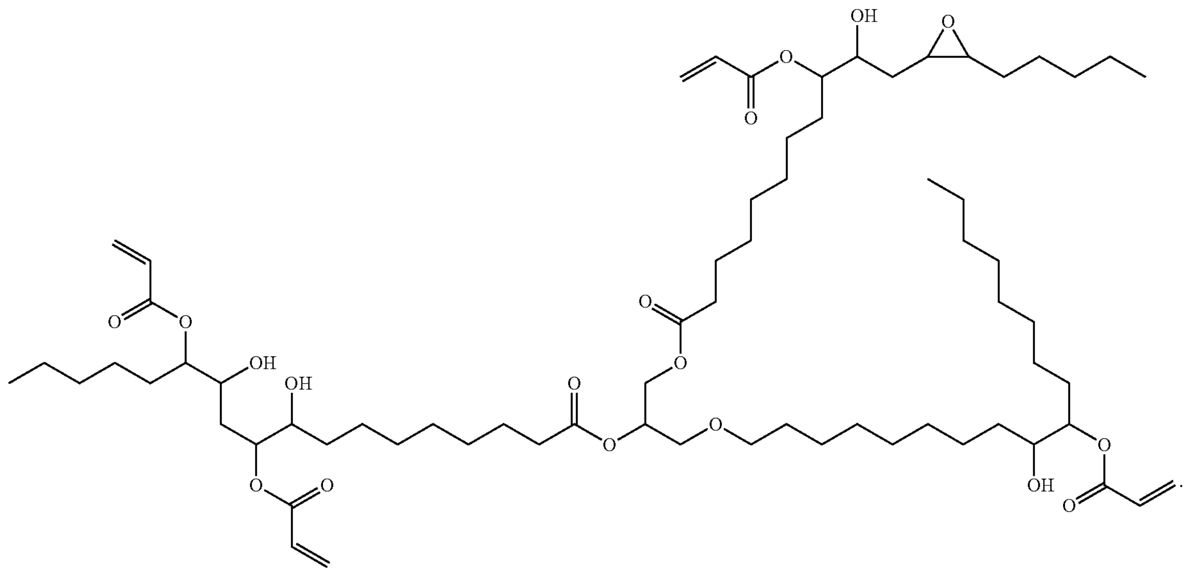 [SMILES: C=CC(=O)OC(CCCCCCCC)C(O)CCCCCCCCOCC(COC(=O)CCCCCCCC(OC(=O)C=C)C(O)CC1OC1CCCCC)OC(=O)CCCCCCCC(O)C(CC(O)C(CCCCC)OC(=O)C=C)OC(=O)C=C]

Another preferred example of a Component (A) is based on soybean oil, linseed oil, or other vegetable oils and has the following representative structure:

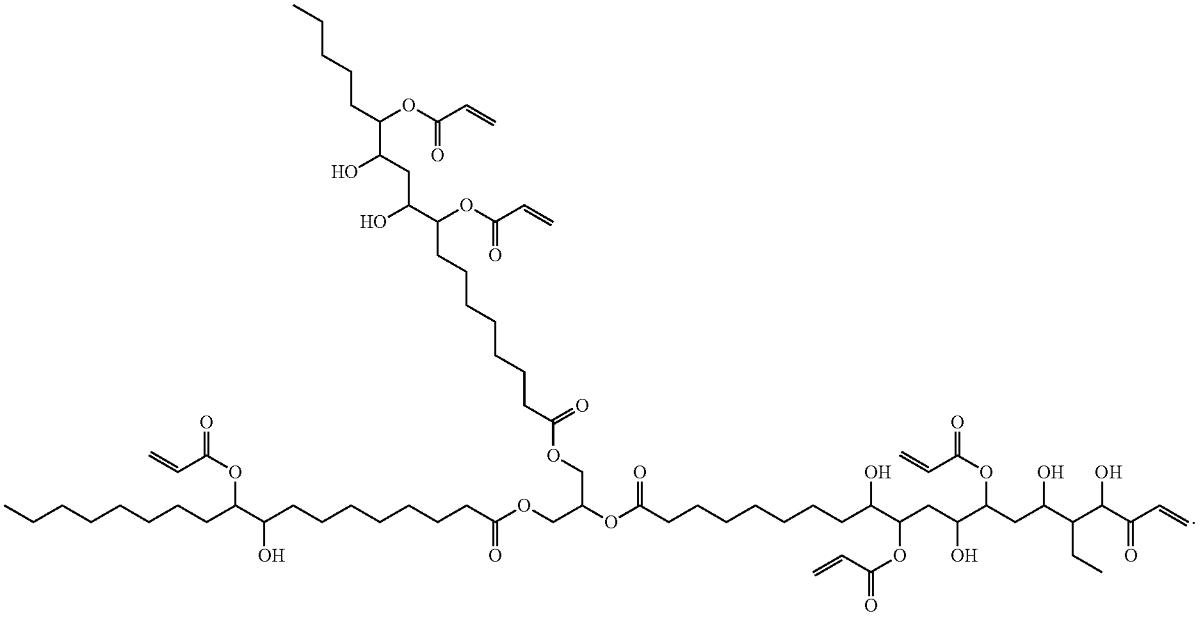 [SMILES: C=CC(=O)OC(CCCCCCCC)C(O)CCCCCCCC(=O)OCC(COC(=O)CCCCCCCC(OC(=O)C=C)C(O)CC(O)C(CCCCC)OC(=O)C=C)OC(=O)CCCCCCCC(O)C(CC(O)C(CC(O)C(CC)C(O)C(=O)C=C)OC(=O)C=C)OC(=O)C=C]

In certain embodiments, Component (A) comprises acrylated epoxidized soybean oil. In some embodiments, Component (A) is prepared from a vegetable oil or mixture thereof, wherein the vegetable oil comprises two or more hydroxyl groups or epoxides. In further embodiments, Component (A) is prepared from linseed oil or soybean oil.

Another preferred example of a Component (A) is trimethylolpropane triacrylate and has the following structure:

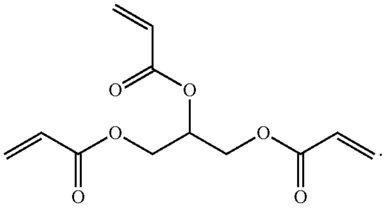 [SMILES: C=CC(=O)OCC(COC(=O)C=C)OC(=O)C=C]

Another preferred example of a Component (A) is glyceryl propoxy triacrylate (also referred to as glycerol propoxylate triacrylate) and has the following structure:

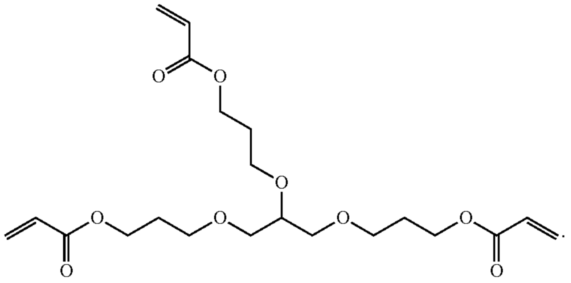 [SMILES: C=CC(=O)OCCCOCC(COCCCOC(=O)C=C)OCCCOC(=O)C=C]

Another preferred example of a Component (A) is a polyether polyol triacrylate and has the following structure:

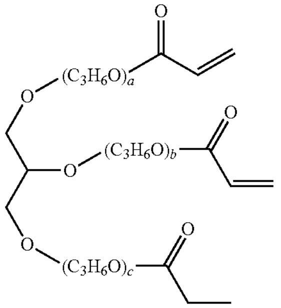

wherein a=an integer from 1 to 30, b=an integer from 1 to 30, and c=an integer from 1 to 30.

Another preferred example of component (A) is methacryloxypropyl terminated polydimethylsiloxane and has the following structure:

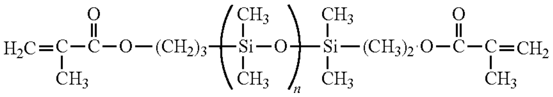

wherein n=an integer between 1 and about 10,000.

Another preferred example of component (A) is (3-acryloxy-2-hydroxypropoxypropyl) terminated polydimethylsiloxane and has the following structure:

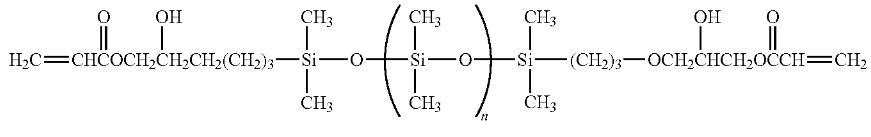

wherein n=an integer between 1 and about 10,000.

In further embodiments, component (A) comprises a metal. Suitably, the metal can serve as a catalyst for the reaction between a Michael acceptor functional group and Michael donor functional group as described herein. In such embodiments, the metal is coordinated by one or more Michael acceptor functional groups of Component (A). In certain embodiments, the metal comprises a zinc ion. In some embodiments, component (A) comprises a coordinated zinc complex. In one embodiment, component (A) comprises zinc acrylate.

A Molecule Comprising a Michael Donor Functional Group, (B)

In some embodiments, a second reactant for making the Michael addition elastomer described herein comprises one or more molecules comprising a Michael donor functional group, wherein the Michael donor functional group comprises one or more Michael active hydrogen atoms in its molecule and is capable of reacting with a Michael acceptor functional group to form a 1,4-addition product. As used herein "one or more molecules" is one or more compounds.

As used herein, a "Michael donor" is a functional group containing at least one Michael active hydrogen atom, which is a hydrogen atom attached to: a carbon atom that is located between two electron-withdrawing groups such as C=O and/or C=N; an oxygen atom; a nitrogen atom; or a sulfur atom. Examples of Michael donor functional groups are malonate esters, acetoacetate esters, malonamides, and acetoacetamides (in which the Michael active hydrogens are attached to the carbon atom between two carbonyl groups); and cyanoacetate esters and cyanoacetamides (in which the Michael active hydrogens are attached to the carbon atom between the carbonyl group and the cyano group); hydroxyl groups; thiol groups; and primary and secondary amines. In some embodiments, the molecule comprises a primary amine. In some embodiments, the molecule comprises a secondary amine. In some embodiments, the molecule comprises a thiol. In some embodiments, the molecule comprises a hydroxyl group. In further embodiments, the molecule comprises a carbon bonded to two Michael donor hydrogen atoms.

One preferred example of component (B) is PRIAMINE™ 1074 from Croda International. Another preferred example of component (B) is PRIAMINE™ 1075 from Croda International. A further preferred example of component (B) is PRIPLAST™ 1074 from Croda International.

Another preferred example of component (B) is PRIPLAST™ 1075 from Croda International and has the representative molecular structure:

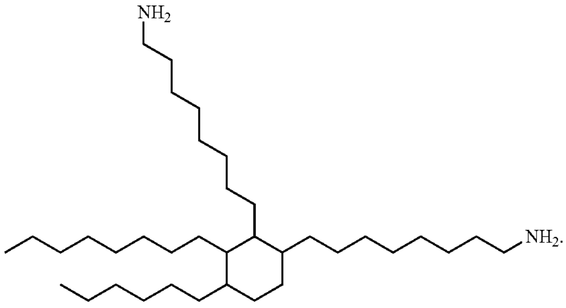 [SMILES: CCCCCCCCC1C(CCCCCC)CCC(CCCCCCCCN)C1CCCCCCCCN]

Another preferred example of component (B) is the aliphatic polyamine hexamethylenediamine and has the structure:

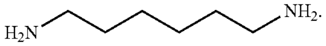

Another preferred example of component (B) is isophorone diamine and has the structure:

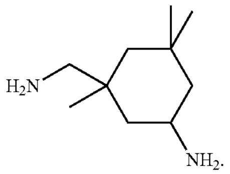

Another preferred example of component (B) is bis(hexamethylene)triamine and has the structure:

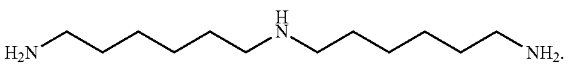

Another preferred example of component (B) is tris(aminoethyl)amine and has the structure:

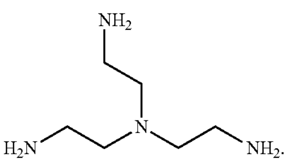

Another preferred example of component (B) is melamine and has the structure:

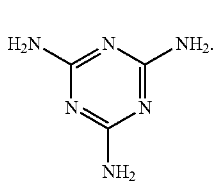

Another preferred example of component (B) is glyceryl poly(oxypropylene) triamine, supplied by Huntsman Corporation as JEFFAMINE® T-403, JEFFAMINE® T-3000, and JEFFAMINE® T-5000 and has the structure:

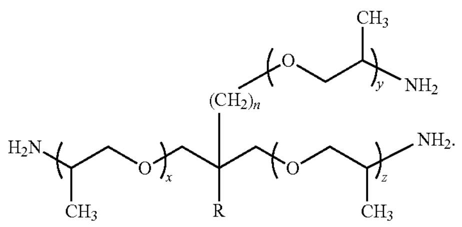

wherein x=an integer from 1 to 30, y=an integer from 1 to 30, and z=an integer from 1 to 30.

Another preferred example of component (B) are polyether diamines supplied by Huntsman Corporation as JEFFAMINE® D Series Diamines and has the following structure:

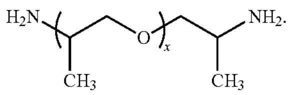

Another preferred example of component (B) are polyether diamines supplied by Huntsman Corporation as JEFFAMINE® ED Series Diamines and has the following structure:

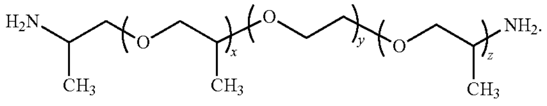

Another preferred example of component (B) is JEFFAMINE® EDR Diamine supplies by Huntsman Corporation has the following structure:

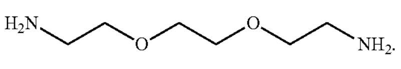

Another preferred example of component (B) is poly (dimethylsiloxane), bis(3-aminopropyl) terminated and has the following structure:

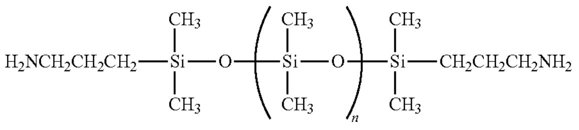

wherein n=is an integer between 1 and about 10,000.

Another preferred example of component (B) is N-ethylaminoisobutyl terminated polydimethylsiloxane and has the following structure:

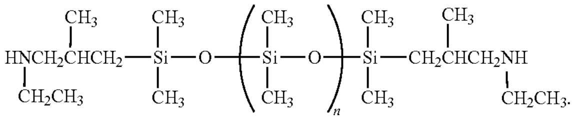

Another preferred example of component (B) is 1,3-benzenedithiol and has the structure:

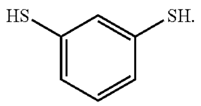

Another preferred example of component (B) is pentaerythritol tetra(3-mercaptopropionate) and has the structure:

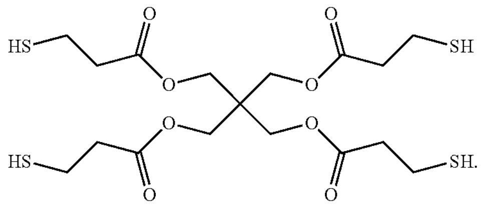 [SMILES: O=C(CCS)OCC(COC(=O)CCS)(COC(=O)CCS)COC(=O)CCS]

Another preferred example of component (B) is dimethiconol and has the structure:

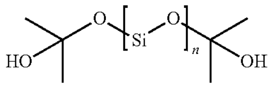

wherein is an integer from n=is an integer from 1 to 100.

Another preferred example of component (B) is mercaptanized soybean oil and has the structure:

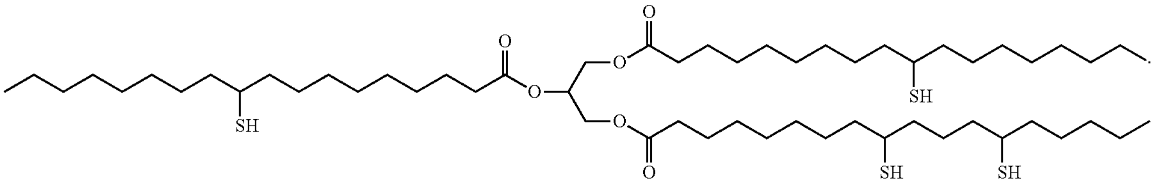

Another preferred example of component (B) is polycaprolactone tetra(3-mercaptopropionate) and has the structure:

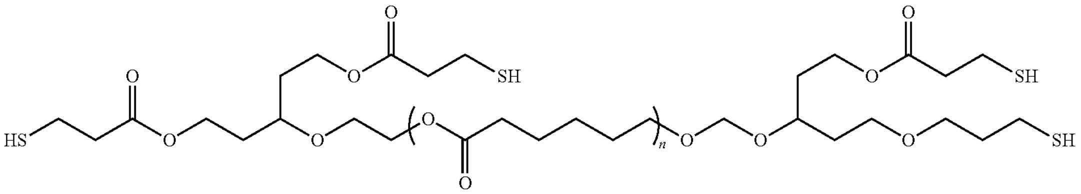

wherein n=is an integer from 1 to 30.

Another preferred example of component (B) is dilinoleic acid/propanediol copolymer and has the representative molecular structure:

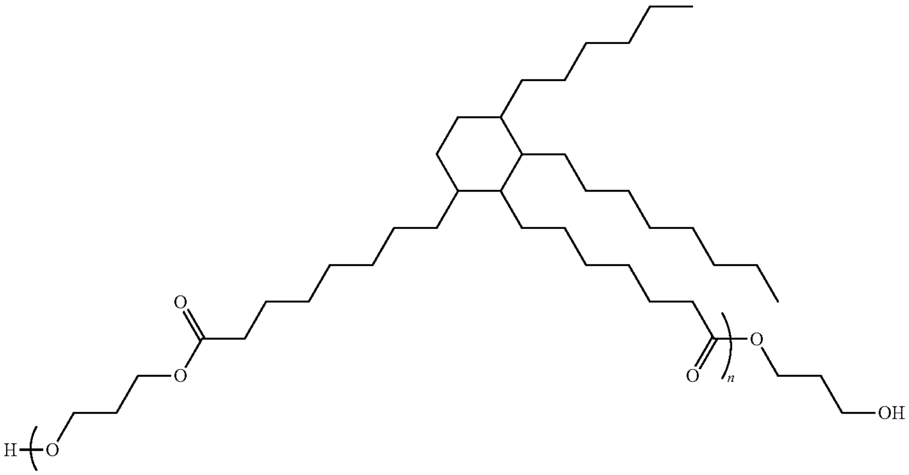

where n=is an integer from 1 to 20.

Another preferred example of component (B) is dilinoleic acid/dilinoleic diol copolymer and has the representative molecular structure:

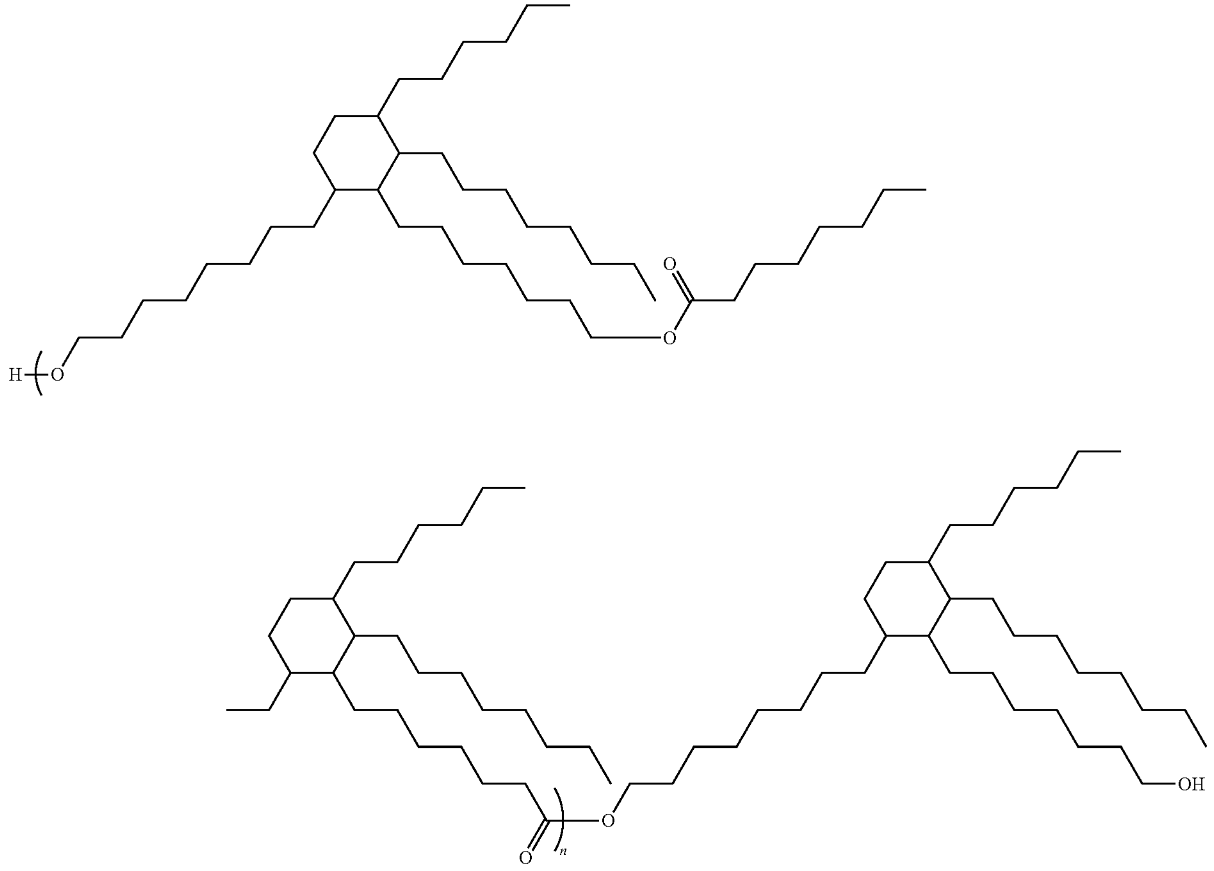

wherein n=is an integer from 1 to 20.

Another preferred example of component (B) is dilinoleic diol and has the representative molecular structure:

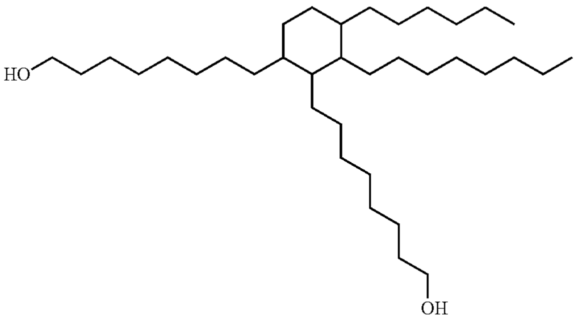 [SMILES: CCCCCCCCC1C(CCCCCC)CCC(CCCCCCCCO)C1CCCCCCCCO]

Another preferred example of component (B) is trimethylolpropane and has the structure:

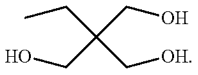

Another preferred example of component (B) is dimethyl malonate and has the structure:

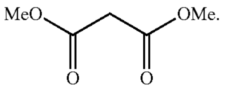

Another preferred example of component (B) is glycerol and has the structure:

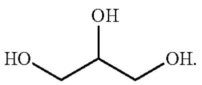

An Optional Reaction Catalyst, (C)

Component (C) can be optionally used to increase the rate of elastomer formation. Amine based nucleophilic catalysts are preferred catalysts for the synthesis of Michael addition elastomer gels due to their favorable reactivity profile. Preferably, 1-methylimidazole is used as the Michael addition catalyst. Base and acid catalysis can also be used, depending on the nature of the reactants. Appropriate Michael addition catalysts include but are not limited to:

Butylamine

Hexylamine

Triethylamine
Triethylenediamine
p-Toluenesulfonic acid
N,N,N',N",N"-Pentamethyldiethylenetriamine
1,2-Dimethylimidazole
N,N,N',N'-Tetramethyl-1,6-hexanediamine
N,N',N'-Trimethylaminoethylpiperazine
1,1'[[3-(dimethylamino)propyl]imino]bispropan-2-ol
20 N,N,N' -Trimethylaminoethylethanolamine
N,N',N"-Tris(3-dimethylaminopropyl)-hexahydro-s-triazine
1,4-diazabicyclo[2.2.2]octane
1,5,7-Triazabicyclo[4.4.0]dec-5-ene
Stannous octoate
Stannous oxalate
Stannous oxide
Stannous chloride
Dioctyltin di(2-hexylhexanoate)-solution
Dioctyltin dithioglycolate
Dioctyltin dilaurate
Dioctyltin oxide blend
Dibutyltin dilaurate
Monobutyl tin tris-(2-ethylhexanoate)
Dioctyltin diketanoate
Dioctyltin diacetate
Dioctyltin oxide
Dibutyltin diacetate
Modified dibutyltin diacetate
Dibutyltin oxide
Monobutyltin dihydroxychloride
Organotin oxide
Monobutyltin oxide
Dioctyltin dicarboxylate
Dioctyltin carboxylate
Dioctyltin stannoxane
Zinc neodecanoate
Zinc octoate
Zinc acetylacetonate
Zinc oxalate
Zinc acetate
Bismuth carboxylates
$Bi(OTf)_3$
Zinc neodecanoate

A Carrier Fluid, (D)

The Michael addition elastomer may be contained in an optional carrier fluid (D). Carrier fluids include any suitable solvent that can be used to prepare the Michael addition elastomer. In exemplary embodiments, the carrier fluid is a "topically acceptable carrier fluid" which is a solvent 30 for topical use on cutaneous surfaces i.e. skin, lips, mucous membranes, etc. Although it is not required, typically the carrier fluid may be the same as the solvent used for conducting the elastomer reaction as described above. The carrier fluid used for the synthesis of the Michael addition elastomer gel and gel paste can be fully, partially, or not bio-based. The carrier fluid, including a topically acceptable carrier fluid, preferably has a viscosity between 1-65 mPas at 20° C. The spreading value of the carrier fluid, including the topically acceptable carrier fluid, is preferably between 500-2500 $mm^2$/10 min. Appropriate topically acceptable carrier fluids for the synthesis of the Michael addition elastomer gel and processing of the Michael addition elastomer gel include but are not limited to esters, triglycerides, hydrocarbons, silicone fluids, and combinations thereof, and include:

Bis-Diglyceryl Polyacyladipate-1
Bis-Diglyceryl Polyacyladipate-2
Butylene Glycol Dicaprylate/Dicaprate
Butyrospermum Parkii Butter
Caprylic/Capric Glycerides
Caprylic/Capric Triglyceride
Caprylic/Capric/Myristic/Stearic Triglyceride
Caprylic/Capric/Succinic Triglyceride
Caprylyl Methicone
Coco-Caprylate/Caprate
Cyclotetrasiloxane
Decamethylcyclopentasiloxane
Decyl Oleate
Dimethiconol
Diphenylsilanediol
Dodecamethylcyclohexasiloxane
Ethyl trisiloxane
Glyceryl Caprylate
Glyceryl Citrate/Lactate/Linoleate/Oleate
Glyceryl Cocoate
Glyceryl Isostearate
Glyceryl Oleate
Glyceryl Ricinoleate
Glyceryl Ricinoleate, Tocopherol
Glyceryl Stearate
Glyceryl Stearate Citrate
Hexamethyldisilazane
Hexamethyldisiloxane
Hydrogenated Coco-Glycerides
Hydrogenated Palm Oil
Hydroxytrimethylsilane
Isopropoxytrimethylsilane
Methylheptyl Isostearate
Octamethylcyclotetrasiloxane
Oleyl Erucate
Olus Oil
Organo-modified Siloxanes
Organosilicone Fluids
PCA Glyceryl Oleate
PEG-6 Caprylic/Capric Glycerides
Phenyltrichlorosilane
Poly(dimethyl siloxane)
Poly(ethylene glycol)-containing siloxanes
Polydimethylsiloxane
Polyglyceryl-2 Caprate
Polyglyceryl-3 Caprate
Polyglyceryl-3 Diisostearate
Polyglyceryl-3 Polyricinoleate
Polyglyceryl-4 Cocoate
Propylene Carbonate
Propylene Glycol Dicaprylate/Dicaprate
Silicone oil
Stearalkonium Bentonite
Stearalkonium Hectorite
Triheptanoin
Trimethyl(bromodifluoromethyl)silane
Trimyristin
Tristearin In some embodiments, the topically acceptable carrier fluid is at a concentration of 0% (w/w) to 99.9% (w/w) of the gel composition. In further embodiments, the topically acceptable carrier fluid is 20% (w/w) to 99.9% (w/w) of the gel composition. In additional embodiments, the topically acceptable carrier fluid is 60% (w/w) to 99.9% (w/w) of the gel composition.

In some embodiments, the topically acceptable carrier fluid comprises triheptanoin, diisooctyl succinate, caprylic/ capric triglyceride, heptyl undecylenate, neopentyl glycol diheptanoate, coco-caprylate/caprate, diisopropyl adipate, isoamyl laurate, isopropyl myristate, jojoba esters, methylheptyl Isostearate, neopentyl glycol diheptanoate, dicaprylin caprylic/capric/myristic/stearic triglyceride, caprylic/capric/succinic triglyceride, ethyl hexyl olivate, C1 5-C16 branched alkanes, C17-C18 branched alkanes, dodecane, hexadecane, squalene, hemisqualane, tetradecane, undecane, tridecane, coconut alkanes, C9-12 alkane, or combinations thereof. In some embodiments, the carrier fluid is triheptanoin, diisooctyl succinate, or caprylic/capric triglyceride.

The Active, (E)

Component (E) is a "pharmaceutically active ingredient," and suitably an active selected from any personal active ingredient or health care active ingredient. As used herein, a "personal care active ingredient" means any compound or mixtures of compounds that are known in the art as additives in the personal care formulations that are typically added for the purpose of treating skin, lips or to provide a cosmetic and/or aesthetic benefit. A "healthcare active ingredient" means any compound or mixtures of compounds that are known in the art to provide a pharmaceutical or medical benefit. Thus, "healthcare active ingredient" includes materials considered as active ingredient or active drug ingredient as generally used and defined by the United States Department of Health & Human Services Food and Drug Administration, contained in Title 21, Chapter I, of the Code of Federal Regulations, Parts 200-299 and Parts 300-499. Thus, pharmaceutically active ingredient can include any component that is intended to furnish pharmacological activity or other direct effect in the diagnosis, cure, mitigation, treatment, or prevention of disease, or to affect the structure or any function of the body of a human or other animals. The phrase can include those components that may undergo chemical change in the manufacture of drug products and be present in drug products in a modified form intended to furnish the specified activity or effect.

Some representative examples of pharmaceutically active ingredients include; drugs, vitamins, minerals; hormones; topical antimicrobial agents such as antibiotic active ingredients, antifungal active ingredients for the treatment of athlete's foot, jockitch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and Sunburn prevention and treatment agents.

Useful pharmaceutically active ingredients for use in processes according to the invention include Vitamins and their derivatives, including "pro-vitamins". Vitamins useful herein include, but are not limited to, Vitamin A, retinol, C-C esters of retinol, Vitamin E, tocopherol, esters of vitamin E, and mixtures thereof. Retinol includes trans-retinol, 1.3-cis-retinol, 11-cis-retinol, 9-cis-retinol, and 3,4-didehydro-retinol, Vitamin C and its derivatives, Vitamin B, Vitamin B. Pro Vitamin B5, panthenol, Vitamin B. Vitamin B2, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl Stearate, ascorbyl glucoside, sodium ascorbyl phosphate, sodium ascorbate, disodium ascorbyl sulfate, potassium (ascorbyl/tocopheryl)phosphate.

Retinol, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are retinylacetate, retinyl palmitate, retinyl propionate, o-tocopherol tocophersolan, tocopheryl acetate, tocopheryl linoleate, tocopheryl nicotinate, and tocopheryl succinate.

The pharmaceutically active ingredient used in processes according to the invention can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, Vincristine, bleomycin sulfate, aurothioglucose, suramin, mebendazole; clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, Salbutamol, guanaben Z, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The active component (E) of the present invention can be a protein, such as an enzyme. The internal inclusion of enzymes in the Michael addition elastomer gel have advantages to prevent enzymes from deactivating and maintain bioactive effects of enzymes for longer time. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha orbeta), lipases, mannanases, cellulases, collagenases, lisozymes, superoxide dismutase, catalase, and mixtures thereof. Said proteases include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Said lipases include, but are not limited to, triacyl-glycerol lipases, monoacyl glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

The pharmaceutically active ingredient may also be a sunscreen agent. The Sunscreen agent can be selected from any Sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; aminobenzoic acid, cinoxate, diethanolamine methoxycinnamate, digalloyl trioleate, dioxybenzone, ethyl 4-bis(Hydroxypropyl) aminobenzoate, glyceryl aminobenzoate, homosalate, lawsone with dihydroxyacetone, menthyl anthranilate, octocrylene, octyl methoxycinnamate, octyl salicylate, oxybenzone, padimate O, phenylbenzimidazole sulfonic acid, red petrolatum, sulisobenzone, titanium dioxide, trolamine salicylate, cetarninosalol, allatoin, PABA, benzalphthalide, benzophenone, benzophenone 1-12, 3-benzylidene camphor, benzylidenecamphor hydrolyzed collagen sulfonamide, benzylidene camphor sulfonic acid, benzyl salicylate, bomelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbene disulfonate, disodium sistyrylbiphenyl triaminotriazine stilbenedisulfonate, disodium distyrylbi phenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycin namate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, octyl methoxycinnamate, octyl salicylate, octyl triazone, PABA, PEG-25 PABA, pentyl dimethyl, PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, zinc dioxide, serium dioxide, TriPABA panthenol, urocanic acid, and VA/crotonates/methacryloxybenzophenone-1 copolymer.

The Sunscreen agent can be a single one or combination of more than one. Alternatively, the Sunscreen agent is a cinnamate based organic compound, or alternatively, the Sunscreen agent is octyl methoxycinnamate, Such as Uvinul R. MC 80 an ester of para-methoxycinnamic acid and 2-ethyl hexanol.

Component (E) may also be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or Sulfur containing compounds, as well as essential oils of natural or synthetic origin. Many of these perfume ingredients are described in detail in standard textbook references such as Perfume and Flavour Chemicals, 1969, S. Arctander, Montclair, N.J.

Fragrances may be exemplified by, but not limited to, perfume ketones and perfume aldehydes. Illustrative of the perfume ketones are buccoxime; isojasmone; methyl beta naphthyl ketone; musk indanone; tonalid/musk plus; Alpha Damascone, Beta-Damascone, Delta-Damascone, Iso Damascone, Damascenone, Damarose, Methyl Dihydrojasmonate, Menthone, Carvone, Camphor, Fenchone, Alpha-lonone, Beta-lonone, Gamma-Methyl So called lonone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or LiveScone, 6-Isopropyldecahydro-2-naphtone, Dimethyloctenone, Freskomenthe, 4-(1-Ethoxyvinyl)-3,3, 5.5,-tetramethyl-Cyclohexanone, Methyl heptenone, 2-(2-(4-Methyl-3 -cyclohexen-1-yl)propyl)-cyclopentanone, 1-(p-Menthen-6(2)-yl)-1-propanone, 4-(4-Hydroxy-3- methoxyphenyl)-2-butanone, 2-Acetyl-3 ,3 -Dimethyl Norbornane, 6,7-Dihydro-1,1,2,3,3 -Pentamethyl-4(5H)-Indanone, 4-Damascol, Dulcinyl or Cassione, Gelsone, Hexylon, Isocyclemone E, Methyl Cyclocitrone, Methyl Lavender-Ketone, Orivon, Para-tertiary-Butyl-Cyclohexanone, Verdone, Delphone, Muscone, Neobutenone, Plica tone, Veloutone, 2,4,4,7-Tetramethyl-oct-6-en-3-one, and Tetrameran.

More preferably, the perfume ketones are selected for their odor character from Alpha Damascone, Delta Damascone, Iso Damascone, Carvone, Gamma-methyl-ionone, Iso-E-Super, 2.4.4.7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal, anisic aldehyde, cymal, ethylvanillin, florhydral, helional, heliotropin, hydroxycitronellal, koavone, lauric aldehyde, lyral, methyl nonyl acetaldehyde, P. T. bucinal, phenyl acetaldehyde, undecylenic aldehyde, vanillin, 2,6,10-trimethyl-9-undecenal, 3-dodecen- 1-al, alpha-n-amyl cinnamic aldehyde, 4-methoxybenzaldehyde, benzaldehyde, 3 -(4-tert-butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al. (3,7-dimethyl-6-octenyl)oxyacetaldehyde, 4-isopropylbenzyaldehyde, 1,2,3,4,5,6,7, 8-octahydro-8,8-dimethyl-2-naphthaldehyde, 2,4-dimethyl-3 -cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)-decylidene-8)-butanal, octahydro-4,7-methano-1H-indenecarboxaldehyde, 3-ethoxy-4-hydroxy benzaldehyde, para-ethyl-alpha,alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3 -cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methylpentyl)-3-cylohexene 1-carboxaldehyde, 7-methoxy-3,7-dimethyloctan-1-al, 2-methyl undecanal, 2-methyl decanal, 1-nonanal, 1-octanal, 2,6,10-trimethyl-5.9-undecadienal, 2-methyl-3-(4-tertbutyl) propanal, dihydrocinnamic aldehyde, 1-methyl-4-(4-methyl 3 -pentenyl)-3 -cyclohexene-1-carbox aldehyde, 5 or 6 methoxyl-hexahydro-4,7-methanoindan-1 or 2-carboxaldehyde, 3,7-dimethyloctan-1-al, 1-undecanal, 10-undecen- 1-al, 4-hydroxy-3-methoxy benzaldehyde, 1-methyl-3-(4-methylpentyl)-3-cyclhexenecarboxaldehyde, 7-hydroxy-3,7-dimethyl octanal, trans-4-decenal, 2,6-nonadienal, paratolylacetaldehyde, 4-methyl phenylacetaldehyde, 2-methyl-4-(2,6, 6-trimethyl-1-cyclohexen-1-yl)-2-butenal, ortho-5 methoxycinnamic aldehyde, 3,5,6-trimethyl-3-cyclohexene carboxaldehyde, 3,7-dimethyl-2-methylene-6-octenal, Phenoxyacetaldehyde, 5,9-dimethyl-4, 8-decadienal, peony aldehyde (6,10-dimethyl-3-oxa-5, 9-undecadien-1-al), hexahydro-4,7-methanoindan-1-carboxaldehyde, 2-methyloctanal, alpha-methyl-4-(1-methylethyl)benzene acetaldehyde, 6,6-dimethyl-2-norpinene-2-propionaldehyde, para-methyl phenoxyacetaldehyde, 2-methyl-3-phenyl-2-propen-1-al, 3,5,5-trimethylhexanal, Hexahydro-8, 8-dimethyl-2-naphthaldehyde, 3 -propyl-bicyclo[2 .2.1-hept-5-ene-2-carbaldehyde, 9-decenal, 3-methyl-5-phenyl-1-pentanal, methylnonyl acetaldehyde, hexanal, trans-2-hexenal, 1-pmenthene-q-carboxaldehyde and mixtures thereof. More preferred aldehydes are selected for their odor character from 1-decanal, benzaldehyde, florhydral, 2,4-dimethyl-3-cyclohexen-1-carboxaldehyde, cis/trans-3,7-dim ethyl-2,6-octadien-1-al, heliotropin, 2,4,6-trimethyl-3- cyclohexene-1-carboxaldehyde, 2,6-nonadienal, alphanamyl cinnamic aldehyde, alpha-n-hexyl cinnamic aldehyde, P.T. Bucinal, lyral, cymal, methylnonyl acetaldehyde, hexanal, trans-2-hexenal, and mixture thereof. In the above list of perfume ingredients, some are commercial names conventionally known to one skilled in the art, and also includes isomers. Such isomers are also suitable for use in the present invention.

Component (E) may also be one or more plant extract. Examples of these components are as follows: *Ashitaba* extract, avocado extract, hydrangea extract, *Althea* extract, *Arnica* extract, *Aloe* extract, apricot extract, apricot kernel extract, *Ginkgo biloba* extract, fennel extract, turmeric Curcuma extract, oolong tea extract, rose fruit extract, *Echinacea* extract, *Scutellaria* root extract, *Phellodendro* bark extract, Japanese Coptis extract, Barley extract, *Hyperium* extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, *Artemisia* extract, *Glycyrrhiza* extract, hibiscustea extract, *Pyracantha fortuneana* Fruit extract, Kiwi extract, *Cinchona* extract, cucumber extract, guanocine, *Gardenia* extract, *Sasa albomarginata* extract, *Sophora* root extract, Walnut extract, Grapefruit extract, *Clematis* extract, *Chlorella* extract, mulberry extract, *Gentiana* extract, black tea extract, yeast extract, burdock extract, rice bran ferment extract, rice germ oil, comfrey extract, collagen, cowberry extract, *Gardenia* extract, *Asiasarum* root extract, Family of Bupleurum extract, umbilical cord extract, *Salvia* extract, *Saponaria* extract, Bamboo extract, *Crataegus* fruit extract, *Zanthoxylum* fruit extract, Shiitake extract, *Rehmannia* root extract, gromwell extract, *Perilla* extract, linden extract, *Filipendula* extract, peony extract, *calamus* root extract, white birch extract, Horsetail extract, *Hedera helix*(Ivy) extract, hawthorn extract,*Sambucus migra* extract, *Achillea millefolium* extract, *Mentha piperita* extract, sage extract, mallow extract, *Cnidium officinale* root extract, Japanese green gen tian extract, Soybean extract, *jujube* extract, thyme extract, tea extract, clove extract, *Gramineae imperata cyrillo* extract, *Citrus unshiu* peel extract Japanese angelica root extract, *Calendula* extract, peach kernel extract, Bitter orange peel extract, *Houttuyna cordata* extract, tomato extract, natto extract, ginseng extract, green tea extract (*Camelliea sine sis*), garlic extract, wild rose extract, hibiscus extract, *Ophio pogon* tuber extract, *Nelumbo nucifera* extract, parsley extract, honey, *Hamamelis* extract, *Parietaria* extract, *Isodonis herba* extract, bisabolol extract, Loquat extract, coltsfoot extract, butterbur extract, Pond cocos wolf extract, extract of butcher's broom, grape extract, propolis extract, lufa extract, safflower extract, peppermintextract, linden tree extract, *Paeonia* extract, hop extract, pine tree extract, horse chestnut extract, Mizu-bashou *Lysichiton camtschatcese* extract, Mukurossi peel extract, Melissa extract, peach extract, corn flower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

The amount of component (E) present in the Michael addition elastomer gel composition may vary, but typically range as follows: 0.05 to 50 wt %, alternatively 1 to 25 wt %, or alternatively 1 to wt %, based on the amount by weight of Michael addition elastomer gel present in the composition, that is total weight of components (A), (B), (C) and (D) in the Michael addition elastomer gel composition.

The active, component (E), may be added to the Michael addition elastomer gel composition either during the making of the Michael addition elastomer (pre-load method), or added after the formation of the Michael addition elastomer gel (post load method).

The pre-load method involves:

I) mixing:

A) a first reactant comprising one or more molecules, wherein each of the one or more molecules comprises two or more Michael acceptor groups;

B) a second reactant comprising one or more molecules, wherein each of the one or more molecules comprises a Michael donor functional group with two or more Michael donor hydrogen atoms, such that the Michael donor functional group is capable of reacting with a Michael acceptor functional group to form a 1,4-addition product;

C) an optional reaction catalyst; and

D) a topically acceptable carrier fluid, at a concentration of 20% (w/w) to 99.9% (w/w) of the gel composition, preferably 60% (w/w) to 99.9% (w/w) of the gel composition; and E) a personal care or healthcare active with the Michael addition elastomer gel to form the Michael addition elastomer gel containing active.

In some embodiments, the Michael donor function group comprises a primary or secondary amine, a thiol, a hydroxyl group or a carbon bonded to two Michael donor hydrogen atoms.

The post-load method involves;

I) mixing:

A) a first reactant comprising one or more molecules, wherein each of the one or more molecules comprises two or more Michael acceptor groups;

B) a second reactant comprising one or more molecules, wherein each of the one or more molecules comprises a Michael donor functional group with two or more Michael donor hydrogen atoms, such that the Michael donor functional group is capable of reacting with a Michael acceptor functional group to form a 1,4-addition product;

C) an optional reaction catalyst; and

D) a topically acceptable carrier fluid, at a concentration of 20% (w/w) to 99.9% (w/w) of the gel composition, preferably 60% (w/w) to 99.9% (w/w) of the gel composition, thereby forming a Michael addition elastomer gel;

II) shearing the Michael addition elastomer gel into a smooth paste; and

III) admixing:

E) a personal care or healthcare active with the Michael addition elastomer gel to form a Michael addition elastomer gel containing active. The personal care active may also be admixed as a component of another mixture with one or more excipients.

In some embodiments, the Michael donor function group comprises a primary or secondary amine, a thiol, a hydroxyl group or a carbon bonded to two Michael donor hydrogen atoms.

The Michael Addition Elastomers

The Michael addition elastomers of the present invention are obtainable as Michael addition reaction products of components (A), (B), and (C) in (D). The term "Michael addition reaction" means the addition of a first reactant containing one or more Michael donor functional groups (such as component (B) to a second reactant containing one or more Michael acceptor functional groups (such as component (A)), optionally in the presence of a catalyst (such as component (C)). The Michael addition reaction may be conducted at room temperature or at elevated temperatures up to 120° C. In some embodiments, the reaction mixture is heated from about 50° C. to about 120° C., preferably to about 100° C. In some embodiments, the molar ratio of the first reactant to the second reactant is 1:1. Alternatively, this ratio can range from 8:1 to 0.5:1. In embodiments, the first reactant comprises an acrylate group (e.g., acrylated epoxidized soybean oil or glycerol propoxylate triacrylate), the second reactant comprises a primary amine (e.g., PRIPLAST™ 1075, PRIMAMINE™ 1074, JEFFAMINE® T-403, JEFFAMINE® T-3000, or poly(dimethylsiloxane), or bis(3-aminopropyl) terminated), and the ratio of primary amines to acrylate groups is about 0.25 to 2. In embodiments, the first reactant comprises an acrylate group (e.g., acrylated epoxidized soybean oil or glycerol propoxylate triacrylate), the second reactant comprises a thiol (e.g., Thiocure-332™, Polymercaptan-358™, or Thiocure-1200V™), and the ratio of thiols to acrylate groups is about 0.25 to 2.

In certain embodiments, the Michael addition reaction is conducted in the presence of a solvent, where the solvent is a topically acceptable carrier fluid (such as component (D)) and can optionally be used without further purification.

Methods for Measuring Hardness of Michael Addition Elastomer Gel Compositions The Michael addition elastomers are prepared in a carrier fluid (as described above as component (D)) to form gelled compositions. The gelled compositions of the present invention may be characterized by their hardness or firmness. Useful tests to characterize the gels are those recommended by the Gelatin Manufacturers Institute of America such as the use of a "Texture Analyzer" (model TAXT2, Stable Micro Systems, Inc., Godalming, England). The gel sample is subjected to a compression test with the Texture Analyzer having a probe with a 5.0 kg load cell. The probe approaches the surface of the gel at a speed of 1 mm/sec and continues compression into the gel to a distance of 5.0 mm. The Texture Analyzer detects the resistance force the probe experiences during the compression test. The force exhibited by the load cell is plotted as a function of time. The hardness of the Michael addition elastomer, gels, and elastomer blends (SEBs) for the purposes of this invention is defined as the resistance force detected by the probe of the "Texture Analyzer" during the compression test. Hardness is characterized as the force at the maximum compression point (i.e. the 5.0 mm compression point into the gel Surface). The average of a total of 3 tests are typically performed for each gel and gels were made in triplicate.

The value obtained for force (in grams) is converted into Newtons (N), by dividing the gram force value by 101.97. (i.e. 1 Newton equals 101.97g force based on the size of the probe used). The second property reported by Texture Analyzer measurement is Area F-T 1:2, in g force sec. This is the area integration of the force vs. test time cure. This property is indicative of a gel network since it indicates ability to sustain resistance to the compression force, which is relevant to elastomers and gels. The value is reported in g force sec and is converted to Newton·sec in SI unit by dividing the value in force-sec by 101.97

The Michael addition elastomer gels of the present invention have a compression hardness of at least 0.5 Newton/$cm^2$, alternatively 1 Newton/$cm^2$, or alternatively 2 Newton/cm2 when measured with a 1.27 cm diameter spherical probe and a 50 g gel sample in a 4-ounce round glass jar.

Gel Paste Compositions Containing the Michael Addition Elastomer

The gelled compositions of the present invention can be used to prepare gel paste or gel blend compositions containing actives by: shearing the Michael addition elastomer gel, as described herein, and combining the sheared Michael addition elastomer gel with additional quantities of the topically acceptable carrier fluid (e.g., Component (D) described herein), and optionally a personal care or health care active (e.g., Component (E) described herein) to form a gel paste or blend composition. The personal care or health care active may also be admixed as a component of another mixture with one or more excipients.

The Michael addition elastomer gel compositions of the present invention may be considered as discrete crosslinked Michael addition elastomer gel particles dispersed in carrier fluids. Thus, the Michael addition elastomer gel compositions are effective rheological thickeners for compatible lower molecular weight solvents. As such they can be used to prepare useful gel blend compositions, such as "gel paste" compositions.

To make such Michael addition elastomer gel pastes, the aforementioned Michael addition elastomer gels of known initial elastomer content (IEC) are sheared to obtain small particle size and further diluted to a final elastomer content (FEC). Shearing, as used herein refers to any shear mixing process, such as obtained from homogenizing, sonolating, or any other mixing processes known in the art as shear mixing. The shear mixing of the Michael addition elastomer gel composition results in a composition having reduced particle size. The subsequent composition having reduced particle size is then further combined with D) the carrier fluid. The carrier fluid may be any carrier fluid as described above, but typically is a linear ester (e.g. heptyl undecylenate), triglyceride (e.g. triheptanoin), or alkane (e.g. isododecane). The technique for combining the topically acceptable carrier fluid with the Michael addition composition having reduced particle size is not critical, and typically involves simple stirring or mixing. The resulting compositions may be considered as a paste, having a viscosity greater than 2,000 cP (mPas), or greater than 100,000 cP (mPas).

Methods for Measuring Viscosity of Michael Addition Elastomer Gel Pastes

In embodiments, the viscosity of the elastomer gel pastes described herein is measured by a Brookfield Helipath™ Stand. The Brookfield Helipath Stand, when used with a suitable Brookfield Viscometer fitted with a special T-bar type spindle, will permit viscosity/consistency measurements in centipoise values for materials having characteristics similar to paste, putty, cream, gelatin, or wax. In embodiments, the viscosity of Michael addition elastomer blends is determined using a Brookfield Model DV-II+Pro Viscometer with Helipath stand (Brookfield Model D) and T-Bar spindles (Brookfield Helipath Spindle Set). The Brookfield Model DV-II+Pro Viscometer with Helipath stand (Brookfield Model D) and T-Bar spindles (Brookfield Helipath Spindle Set) can be purchased from Brookfield Engineering Laboratories, Inc. (11 Commerce Boulevard Middleboro, Mass., USA). In some embodiments, the measuring is conducted with a sample size of 50 g in a 4-ounce round jar. In further embodiments, the sample is prepared by removing air bubbles from the sample, e.g., centrifuged then placed under vacuum for about two hours. In some embodiments, the sample is condition for at least about 4 hours at 25° C. following the air bubble removal. In embodiments, the measurement is taken according to the typical procedure for a Helipath spindle. In general, spindle 93 (T-bar spindle E) is used and the standard setting for rpm can be 6.0 or 6.5. The spindle speed can be maintained at constant 6.0 rpm or 6.5 rpm.

Topical formulations comprising the gel compositions or gel pastes are also provided herein. In such formulations, the gel compositions or gel pastes are suitably used as thickeners or stabilizers for the topical formulations. Other components of the topical formulations are known in the art, and can include for example, various components such as emulsion stabilizers, emulsifiers skin conditioners, suspending agents, surfactants, etc. The amounts of these additional components can be on the order of about 0.01% to about 50% by weight.

As used herein an "emulsion stabilizer" refers to a composition that aids in keeping an emulsion from separating into its oil and aqueous components. In embodiments, the emulsion stabilizer utilized in the formulations described herein is a naturally derived gum or a modified gum or natural mineral. Exemplary emulsion stabilizers include, but are not limited to, acacia, cellulose, crystalline cellulose, gellan, guar, locust (carob) bean, xanthan, magnesium aluminum silicate, bentonite or hectorite clays and the like, including combinations thereof.

As used herein a "skin conditioner" refers to a composition that acts as a lubricant on the surface of the skin or a composition that increases the water content of the surface of the skin. Exemplary skin conditioners for use in the formulations include, but are not limited to, adipate esters, alkyl benzoates, fatty acid esters of C8 or greater, esterified erucates, laurates, neopentanoates, salicylates, stearates, triglycerides, carbonates, glycols, glycerin, mineral oils and the like, including combinations thereof.

As used herein an "emulsifier" refers to a composition that aids in the formation of an oil in water, or a water in oil, emulsion. Exemplary emulsifiers for use in the formulations include, but are not limited to, polysorbates, ethoxylated fatty acids, fatty acids neutralized with sodium hydroxide, potassium hydroxide or amines, substituted glucosides, sodium lauryl and lauryl ether sulfates, ethoxylated esters, lecithin and lecithin derivatives and the like, including combinations thereof.

As used herein a "suspending agent" refers to a composition that modifies the interface between solid particles and a liquid medium to improve the particles' resistance to coming together and falling out of solution. Exemplary suspending agents for use in the formulations include, but are not limited to, hydroxy stearic acid, polyhydroxystearic acid, sodium polyacrylate polymers, methyl methacrylate crosspolymers and the like, including combinations thereof.

As used herein a "surfactant" refers to a composition that prevents phase separation of the gel paste. Exemplary surfactants for use in the formulations include, but are not limited to, polyglyceryl-6 polyricinoleate, polysorbate 80, ethylhexyl hydroxystearate, glyceryl ricinoleate, glyceryl triacetyl ricinoleate, glyceryl triacetyl hydroxystearate, polyglyceryl-10 hexaoleate (and) polyglyceryl-6 polyricinoleate, capryloyl glycerin/sebacic acid copolymer, including combinations thereof.

In additional embodiments, the Michael addition elastomer or Michael addition elastomer gel composition can be utilized in solid-based formats, including for example, as a foot conforming shoe insert or shoe sole.

The Michael addition elastomer or Michael addition elastomer gel composition can also be used as medically acceptable gels, including for example, medical implants or portions of implants, including as cartilage replacements, bone replacements, etc.

Exemplary Embodiments

1. A Michael addition elastomer of Formula I:

Formula I

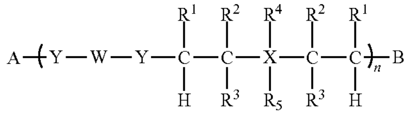

wherein:

n is 2 to m;

A is an end group selected from hydrogen, acrylate, acrylamide, methacrylate, vinyl sulfone, maleimide, sulfhydryl, hydroxyl, amine, malonate, and nitroalkane;

B is an end group selected from hydrogen, acrylate, acrylamide, methacrylate, vinyl sulfone, maleimide, sulfhydryl, hydroxyl, amine, malonate, and nitroalkane;

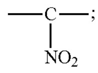

Y is carbonyl, sulfone, or

W is a $C_1$-$C_{30}$ substituted or unsubstituted linear or branched alkyl group, aliphatic group, cycloaliphatic group, or aryl group, optionally comprising a heteroatom;

X is nitrogen or carbon;

$R^1$ is independently hydrogen or a $C_1$-$C_{30}$ substituted or unsubstituted linear or branched alkyl group, aliphatic group, cycloaliphatic group, or aryl group, optionally comprising a heteroatom;

$R^2$ and $R^3$ are independently hydrogen or a $C_1$-$C_{30}$ substituted or unsubstituted linear or branched alkyl group, aliphatic group, cycloaliphatic group, or aryl group, optionally comprising a heteroatom, and also optionally bonded to Y in the case of a maleimide adduct;

$R^4$ is independently hydrogen or a $C_1$-$C_{30}$ substituted or unsubstituted linear or branched alkyl group, aliphatic group, cycloaliphatic group, or aryl group, optionally comprising a heteroatom;

$R^5$ is independently hydrogen or a $C_1$-$C_{30}$ substituted or unsubstituted linear or branched alkyl group, aliphatic group, cycloaliphatic group, or aryl group, optionally comprising a heteroatom, and in the case where X is nitrogen $R^5$ is a lone pair of electrons;

wherein m is a whole integer between 3 and 1,000,000,000,000.

2. A gel composition comprising a Michael addition elastomer prepared from the reaction of:

a) a first reactant comprising one or more molecules, wherein each of the one or more molecules comprises two or more Michael acceptor functional groups, optionally wherein the two or more Michael acceptor functional groups are coordinated by zinc, and wherein the first reactant optionally comprises an OH, SH or NH functional group at a vicinal position to each of the Michael acceptor functional groups;

b) a second reactant comprising one or more molecules, wherein each of the one or more molecules comprises a Michael donor functional group capable of reacting with the two or more Michael acceptor functional groups to form 1,4-addition products, wherein the Michael donor functional group comprises a primary or secondary amine, a thiol, a hydroxyl group, or a carbon bonded to two Michael donor hydrogen atoms;

c) an optional reaction catalyst; and d) a topically acceptable carrier fluid, at a concentration of 0% (w/w) to 99.9% (w/w) of the gel composition, preferably 20% (w/w) to 99.99% (w/w) of the gel composition.

3. The gel composition of embodiment 2, wherein the topically acceptable carrier fluid is selected from the group consisting of esters, triglycerides, hydrocarbons, silicone fluids, and combinations thereof.

4. The gel composition of embodiment 2, wherein the topically acceptable carrier fluid is selected from triheptanoin, diisooctyl succinate, caprylic/capric triglyceride, heptyl undecylenate, neopentyl glycol diheptanoate, cococaprylate/caprate, diisopropyl adipate, isoamyl laurate, isopropyl myristate, jojoba esters, methylheptyl Isostearate, neopentyl glycol diheptanoate, dicaprylin caprylic/capric/myristic/stearic triglyceride, caprylic/capric/succinic triglyceride, ethyl hexyl olivate, C15-C16 branched alkanes, C17-C18 branched alkanes, dodecane, hexadecane, squalene, hemisqualane, tetradecane, undecane, tridecane, coconut alkanes, C9-12 alkane, and combinations thereof.

5. The gel composition of embodiment 2, further comprising a pharmaceutically active ingredient dissolved in the topically acceptable carrier fluid.

6. The gel composition of embodiment 2, further comprising a pharmaceutically active ingredient incorporated in the gel.

7. The gel composition of embodiment 2, wherein the first reactant comprises acrylated epoxidized soybean oil, the second reactant is PRIPLAST® 1075, wherein the ratio of primary amines to acrylate groups is about 0.25 to 2, and the carrier fluid is triheptanoin, diisooctyl succinate, or caprylic/capric triglyceride.

8. The gel composition of embodiment 2, wherein the first reactant comprises acrylated epoxidized soybean oil, the second reactant is PRIPLAST® 1074, wherein the ratio of primary amines to acrylate groups is about 0.25 to 2, and the carrier fluid is triheptanoin, diisooctyl succinate, or caprylic/capric triglyceride.

9. The gel composition of embodiment 2, wherein the first reactant comprises acrylated epoxidized soybean oil, the second reactant is JEFFAMINE® T-403, wherein the ratio of primary amines to acrylate groups is about 0.25 to 2, and the carrier fluid is triheptanoin, diisooctyl succinate, or caprylic/capric triglyceride.

10. The gel composition of embodiment 2, wherein the first reactant comprises acrylated epoxidized soybean oil, the second reactant is JEFFAMINE® T-3000, wherein the ratio of primary amines to acrylate groups is about 0.25 to 2, and the carrier fluid is triheptanoin, diisooctyl succinate, or caprylic/capric triglyceride.

11. The gel composition of embodiment 2, wherein the first reactant comprises acrylated epoxidized soybean oil, the second reactant is poly(dimethylsiloxane), bis(3-aminopropyl) terminated, wherein the ratio of primary amines to acrylate groups is about 0.25 to 2, and the carrier fluid is triheptanoin, diisooctyl succinate, or caprylic/capric triglyceride.

12. The gel composition of embodiment 2, wherein the first reactant comprises glycerol propoxylate triacrylate, the second reactant is PRIPLAST® 1075 , wherein the ratio of primary amines to acrylate groups is about 0.25 to 2, and the carrier fluid is triheptanoin, diisooctyl succinate, or caprylic/capric triglyceride.

13. The gel composition of claim 2, wherein the first reactant comprises glycerol propoxylate triacrylate, the second reactant is PRIPLAST®1074, wherein the ratio of primary amines to acrylate groups is about 0.25 to 2 equivalents of primary amines to acrylate groups is used, and the carrier fluid is triheptanoin, diisooctyl succinate, or caprylic/capric triglyceride.

14. The gel composition of claim 2, wherein the first reactant comprises glycerol propoxylate triacrylate, the second reactant is JEFFAMINE® T-403 , wherein the ratio of primary amines to acrylate groups is about 0.25 to 2, and the carrier fluid is triheptanoin, diisooctyl succinate, or caprylic/capric triglyceride.

15. The gel composition of claim 2, wherein the first reactant comprises glycerol propoxylate triacrylate, the second reactant is JEFFAMINE® T-3000, wherein the ratio of primary amines to acrylate groups is about 0.25 to 2, and the carrier fluid is triheptanoin, diisooctyl succinate, or caprylic/capric triglyceride.

16. The gel composition of claim 2, wherein the first reactant comprises glycerol propoxylate triacrylate, the second reactant is poly(dimethylsiloxane), bis(3-aminopropyl) terminated, wherein the ratio of primary amines to acrylate groups is about 0.25 to 2, and the carrier fluid is triheptanoin, diisooctyl succinate, or caprylic/capric triglyceride.

17. The gel composition of claim 2, wherein the first reactant comprises acrylated epoxidized soybean oil, the second reactant is Thiocure-332™, wherein the ratio of thiols to acrylate groups is about 0.25 to 2, and the carrier fluid is triheptanoin, diisooctyl succinate, or caprylic/capric triglyceride.

18. The gel composition of claim 2, wherein the first reactant comprises glycerol propoxylate triacrylate, the second reactant is Polymercaptan-358™, wherein the ratio of thiols to acrylate groups is about 0.25 to 2, and the carrier fluid is triheptanoin, diisooctyl succinate, or caprylic/capric triglyceride.

19. The gel composition of claim 2, wherein the first reactant comprises glycerol propoxylate triacrylate, the second reactant is Thiocure-333™, wherein the ratio of thiols to acrylate groups is about 0.25 to 2, and the carrier fluid is triheptanoin, diisooctyl succinate, or caprylic/capric triglyceride.

20. The gel composition of claim 2, wherein the first reactant comprises glycerol propoxylate triacrylate, the second reactant is Thiocure-1200™, wherein the ratio of thiols to acrylate groups is about 0.25 to 2, and the carrier fluid is triheptanoin, diisooctyl succinate, or caprylic/capric triglyceride.

21. The gel composition of embodiment 2, wherein the first reactant is zinc acrylate.

22. A method of making a Michael addition elastomer of embodiment 1 comprising:

i) mixing a first reactant comprising one or more molecules, wherein each of the one or more molecules comprises two or more Michael acceptor functional groups and a second reactant comprising one or more molecules, wherein each of the one or more molecules comprises a Michael donor functional group, wherein the Michael donor function group comprises a primary or secondary amine, a thiol, a hydroxyl group, or a carbon bonded to two Michael donor hydrogen atoms;

ii) optionally diluting the first and second reactants in a solvent;

iii) optionally adding a reaction catalyst; and iv) optionally heating the reaction mixture from about 50° C. to about 120° C., preferably to about 100° C., to form the Michael addition elastomer.

23. A method of making the Michael addition elastomer gel of embodiment 2 comprising:

i) mixing the first reactant and the second reactant in a topically acceptable carrier fluid to form a reaction mixture, wherein the first and second reactants are present in a concentration of about 50% (w/w);

ii) optionally adding a reaction catalyst; and iii) optionally heating the reaction mixture from about 50° C. to about 120° C., preferably to about 100° C., to form the Michael addition elastomer.

24. The method of embodiment 22, wherein the topically acceptable carrier fluid is selected from the group consisting of esters, triglycerides, hydrocarbons, silicone fluids, and combinations thereof.

25. The method of embodiment 22, wherein the topically acceptable carrier fluid is selected from triheptanoin, diisooctyl succinate, caprylic/capric triglyceride, heptyl undecylenate, neopentyl glycol diheptanoate, coco-caprylate/caprate, diisopropyl adipate, isoamyl laurate, isopropyl myristate, jojoba esters, methylheptyl Isostearate, neopentyl glycol diheptanoate, dicaprylin caprylic/capric/myristic/stearic triglyceride, caprylic/capric/succinic triglyceride, ethyl hexyl olivate, C15-C16 branched alkanes, C17-C18 branched alkanes, dodecane, hexadecane, squalene, hemisqualane, tetradecane, undecane, tridecane, coconut alkanes, C9-12 alkane, and combinations thereof.

26. The method of embodiment 22, further comprising dissolving a pharmaceutically active ingredient in the topically acceptable carrier fluid.

27. The method of embodiment 22, wherein the second reactant containing the Michael donors comprises one or more amine, thiol, hydroxyl, or a carbon atom that is located between two electron-withdrawing groups such as C═O and/or C═N; an oxygen atom and has two hydrogen atoms attached.

28. The method of embodiment 22, further comprising preparing the first reactant from a vegetable oil or mixture thereof, wherein the vegetable oil comprises two or more hydroxyl groups or epoxides.

29. The method of embodiment 22, further comprising preparing the first reactant molecule with two or more Michael acceptor functional groups from linseed oil, soybean oil, or other vegetable oils.

30. A Michael addition elastomer gel paste made by:

i) shearing the Michael addition elastomer of embodiment 2;

ii) optionally adding additional quantities of the topically acceptable carrier fluid during shearing to produce a gel paste composition; and iii) optionally adding a pharmaceutically active ingredient.

31. A topical formulation comprising:

the gel composition of embodiment 5 or embodiment 6, wherein the pharmaceutically active ingredient is a personal care active ingredient or a healthcare active ingredient.

32. A topical formulation comprising:

the Michael addition elastomer gel paste of embodiment 30, comprising a personal care active ingredient or a healthcare active ingredient.

33. A gel composition comprising:

a) a first reactant comprising one or more molecules, wherein each of the one or more molecules comprises two or more Michael acceptor functional groups;

b) a second reactant comprising one or more molecules, wherein each of the one or more molecules comprises a Michael donor functional group capable of reacting with a Michael acceptor group to form 1,4-addition products, wherein the Michael donor functional group comprises a primary amine or a carbon bonded to two Michael donor hydrogen atoms;

c) an optional reaction catalyst; and d) a topically acceptable carrier fluid, at a concentration of 0% (w/w) to 99.9% (w/w) of the gel composition, preferably 20% (w/w) to 99.9% (w/w) of the gel composition.

34. A foot conforming shoe insert or shoe sole comprising:

the Michael addition elastomer of embodiment 1 or the gel composition of embodiment 33.

35. A medical medically acceptable gel comprising:

the Michael addition elastomer of embodiment 1 or the gel composition of embodiment 33.

36. A topical formulation comprising:

the Michael addition elastomer of embodiment 1.

37. A gel composition comprising the Michael addition elastomer of embodiment 1 and a topically acceptable carrier fluid, at a concentration of 0% (w/w) and 99.9% (w/w) of the gel composition, preferably 60% (w/w) and 99.9% (w/w) of the gel composition.

38. A method of making a Michael addition elastomer gel paste comprising the steps of:

i) shearing the gel composition of embodiment 37;

ii) optionally adding quantities of the topically acceptable carrier fluid during shearing to produce a gel paste composition; and iii) optionally adding a pharmaceutically active ingredient.

39. A Michael addition elastomer gel paste prepared by the method of embodiment 38.

40. A topical formulation comprising the gel composition of embodiment 38 or the Michael addition elastomer gel paste of embodiment 39.

EXAMPLES

Example 1— Preparation of Glycerol Propoxylate Triacrylate/Priamine™ 1075 aza-Michael Elastomer with an Acrylate/Primary Amine Functional Group Ratio of 1:1

To a stainless steel or glass reaction vessel was added caprylic/capric triglyceride (279.7 grams) and Priamine™ 1075 (Croda International Plc, 36 grams, 1 equivalent of primary amines to acrylate groups). The mixture was stirred vigorously for 3 minutes before the addition of glycerol propoxylate triacrylate (19.26 grams). The resultant mixture was stirred vigorously for an additional 5 minutes. 50 grams of the mixture was poured into a 4-ounce glass jar. The reaction mixture and the 50-gram sample were covered and left to stand at room temperature in the dark. After 403 hours a colorless transparent rubber had formed. The hardness of the 50-gram sample was 423 grams force, as determined using a Stable Micro Systems Texture Analyzer with a 5-kilogram load cell fitted with a TA-18B Stable Micro Systems probe, which was inserted 5 mm into the rubber surface.

The aza-Michael elastomeric rubber was broken into smaller pieces, placed in a metal container, and caprylic/capric triglyceride was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 2—Preparation of Glycerol Propoxylate Triacrylate/Priamine™ 1075 aza-Michael Elastomer with an Acrylate/Primary Amine Functional Group Ratio of 1:0.5

To a stainless steel or glass reaction vessel was added triheptanoin (261.6 grams) and glycerol propoxylate triacrylate (30.68 g). The mixture was stirred vigorously for 5 minutes before the addition of Priamine™ 1075 (Croda International Plc, 28.69 grams, 0.5 equivalent of primary amines to acrylate groups). The resultant mixture was stirred vigorously an additional 5 minutes. 50 grams of the mixture was poured into a 4-ounce glass jar. The remainder of the reaction mixture and the 50-gram sample were covered and heated to 55° C. After 69 hours a colorless transparent rubber had formed. The hardness of the 50-gram sample was 301 grams force, as determined using a Stable Micro Systems Texture Analyzer with a 5-kilogram load cell fitted with a TA-18B Stable Micro Systems probe, which was inserted 5 mm into the rubber surface.

The aza-Michael elastomeric rubber was broken into smaller pieces, placed in a metal container, and triheptanoin was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 3—Preparation of Glycerol Propoxylate Triacrylate/JEFFAMINE° T-403 aza-Michael Elastomer with an Acrylate/Primary Amine Functional Group Ratio of 1:1

To a stainless steel or glass reaction vessel was added diisooctyl succinate (215.0 grams) and glycerol propoxylate triacrylate (44.00 grams). The mixture was stirred vigorously for 3 minutes before the addition of JEFFAMINE® T-403 (Huntsman Corporation, 48.13 grams, 1 equivalent of primary amines to acrylate groups). The resultant mixture was stirred vigorously for an additional 7 minutes. 50 grams of the mixture was poured into a 4-ounce glass jar. The remainder of the reaction mixture and the 50-gram sample were covered and heated to 50° C. After 90 hours a colorless transparent rubber had formed. The hardness of the 50-gram sample was 601 grams force, as determined using a Stable Micro Systems Texture Analyzer with a 5-kilogram load cell fitted with a TA-18B Stable Micro Systems probe, and inserted 5 mm into the rubber surface.

The aza-Michael elastomeric rubber was broken into smaller pieces, placed in a metal container, and diisooctyl succinate was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 4—Preparation of Glycerol Propoxylate Triacrylate/JEFFAMINE® T-403 aza-Michael Elastomer with an Acrylate/Primary Amine Functional Group Ratio of 1:0.5

To a stainless steel or glass reaction vessel was added diisooctyl succinate (214.4 grams) and glycerol propoxylate triacrylate (59.40 grams). The mixture was stirred vigorously for 3 minutes before the addition of JEFFAMINE® T-403 (Huntsman Corporation, 32.49 grams, 0.5 equivalent of primary amines to acrylate groups). The resultant mixture was stirred vigorously for an additional 7 minutes. 50 grams of the mixture was poured into a 4-ounce glass jar. The remainder of the reaction mixture and the 50-gram sample were covered and heated to 75° C. After 93 hours a colorless transparent rubber had formed. The hardness of the 50-gram sample of rubber was 241 grams force, as determined using a Stable Micro Systems Texture Analyzer with a 5-kilogram load cell fitted with a TA-18B Stable Micro Systems probe and inserted 5 mm into the rubber surface.

The aza-Michael elastomeric rubber was broken into smaller pieces, placed in a metal container, and diisooctyl succinate was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 5—Preparation of Glycerol Propoxylate Triacrylate/Poly(Dimethylsiloxane), bis(3-Aminopropyl) Terminated aza-Michael Elastomer with an Acrylate/Primary Amine Functional Group Ratio of 1:1

To a stainless steel or glass reaction vessel was added diisooctyl succinate (214.7 grams) and glycerol propoxylate triacrylate (21.27 grams). The mixture was stirred vigorously for 3 minutes. DMS A12 (Gelest Inc., 70.74 grams, 1 equivalent of primary amines to acrylate groups) was added and the mixture was stirred vigorously for an additional 7 minutes. 50 grams of the mixture was poured into a 4-ounce glass jar. The remainder of the reaction mixture and the 50-gram sample were covered and heated to 50° C. After 96 hours a colorless transparent rubber had formed. The hardness of the 50-gram sample of rubber was 305.0 grams force, as determined using a Stable Micro Systems Texture Analyzer with a 5-kilogram load cell fitted with a TA-18B Stable Micro Systems probe and inserted 5 mm into the rubber surface.

The aza-Michael elastomeric rubber was broken into smaller pieces, placed in a metal container, and diisooctyl succinate was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 6—Preparation of Glycerol Propoxylate Triacrylate/Poly(Dimethylsiloxane), bis(3-aminopropyl) Terminated aza-Michael Elastomer with an Acrylate/Primary Amine Functional Group Ratio of 1:0.5

To a stainless steel or glass reaction vessel was added diisooctyl succinate (212.49 grams) and glycerol propoxylate triacrylate (34.20 grams). The mixture was stirred vigorously for 3 minutes. DMS A12 (Gelest Inc., 56.87 grams, 0.5 equivalent of primary amines to acrylate groups) was added and the mixture was stirred vigorously for an additional 7 minutes. 50 grams of the mixture was poured into a 4-ounce glass jar. The remainder of the reaction mixture and the 50-gram sample were covered and heated to 75° C. After 163 hours a colorless transparent rubber had formed. The hardness of the 50-gram sample of rubber was 33.7 grams force, as determined using a Stable Micro Systems Texture Analyzer with a 5-kilogram load cell fitted with a TA-18B Stable Micro Systems probe and inserted 5 mm into the rubber surface.

The aza-Michael elastomeric rubber was broken into smaller pieces, placed in a metal container, and diisooctyl succinate was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 7—Preparation of Acrylated Epoxidized Soybean Oil/Priamine™ 1074 aza-Michael Elastomer with an Acrylate/Primary Amine Functional Group Ratio of 1:1

To a stainless steel or glass reaction vessel was added triheptanoin (256.7 grams) and acrylated epoxidized soybean oil (30.87 grams). The mixture was stirred vigorously for 10 minutes before the addition of Priamine™ 1074 (Croda International Plc, 16.21 grams, 1 equivalent of primary amines to acrylate groups). The resultant mixture was stirred vigorously for an additional 5 minutes. 50 grams of the mixture was poured into a 4-ounce glass jar. The remainder of the reaction mixture and the 50-gram sample were covered and heated to 80° C. After 22 hours a transparent rubber had formed. The hardness of the 50-gram sample of rubber was 298.2 grams force, as determined using a Stable Micro Systems Texture Analyzer with a 5-kilogram load cell fitted with a TA-18B Stable Micro Systems probe and inserted 5 mm into the gel surface.

The aza-Michael elastomeric rubber was broken into smaller pieces, placed in a metal container, and triheptanoin was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 8—Preparation of Acrylated Epoxidized Soybean Oil/Priamine™ 1075 aza-Michael Elastomer with an Acrylate/Primary Amine Functional Group Ratio of 1:0.5

To a stainless steel or glass reaction vessel was added triheptanoin (251.4 grams) and acrylated epoxidized soybean oil (50.47 grams). The mixture was stirred vigorously for 7 minutes, before the addition of Priamine™ 1075 (Croda International Plc, 12.38 grams, 0.5 equivalent of primary amines to acrylate groups). The resultant mixture was stirred vigorously for an additional 3 minutes. 50 grams of the mixture was poured into a 4-ounce glass jar. The remainder of the reaction mixture and the 50-gram sample were covered and heated to 75° C. After 19 hours a transparent rubber had formed. The hardness of the 50-gram sample of rubber was 262 grams force, as determined using a Stable Micro Systems Texture Analyzer with a 5-kilogram load cell, fitted with a TA-18B Stable Micro Systems probe, and inserted 5 mm into the gel surface.

The aza-Michael elastomeric rubber was broken into smaller pieces, placed in a metal container, and triheptanoin was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 9—Preparation of Acrylated Epoxidized Soybean Oil/JEFFAMINE° T-403 aza-Michael Elastomer with an Acrylate/Primary Amine Functional Group Ratio of 1:1

To a stainless steel or glass reaction vessel was added triheptanoin (258.4 grams) and acrylated epoxidized soybean oil (49.29 grams). The mixture was stirred vigorously for 10 minutes before the addition of JEFFAMINE® T-403 (Huntsman Corporation, 15.31 grams, 1 equivalent of primary amines to acrylate groups). The resultant mixture was stirred vigorously for an additional 5 minutes. 50 grams of the mixture was poured into a 4-ounce glass jar. The remainder of the reaction mixture and the 50-gram sample were covered and heated to 80° C. After 19 hours a transparent rubber had formed. The hardness of the 50-gram sample of rubber was 193 grams force, as determined using a Stable Micro Systems Texture Analyzer with a 5-kilogram load cell fitted with a TA-18B Stable Micro Systems probe and inserted 5 mm into the gel surface.

The aza-Michael elastomeric rubber was broken into smaller pieces, placed in a metal container, and triheptanoin was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 10—Preparation of Acrylated Epoxidized Soybean Oil/JEFFAMINE° T-403 aza-Michael Elastomer with an Acrylate/Primary Amine Functional Group Ratio of 1:0.5

To a stainless steel or glass reaction vessel was added triheptanoin (214.0 grams) and acrylated epoxidized soybean oil (80.04 grams). The mixture was stirred vigorously for 10 minutes before the addition of JEFFAMINE® T-403 (Huntsman Corporation, 11.66 grams, 0.5 equivalent of primary amines to acrylate groups). The resultant mixture was stirred vigorously for an additional 5 minutes. 50 grams of the mixture was poured into a 4-ounce glass jar. The remainder of the reaction mixture and the 50-gram sample were covered and heated to 80° C. After 22 hours a transparent rubber was formed. The hardness of the 50-gram sample of rubber was 83 grams force, as determined using a Stable Micro Systems Texture Analyzer with a 5-kilogram load cell fitted with a TA-18B Stable Micro Systems probe and inserted 5 mm into the gel surface.

The aza-Michael elastomeric rubber was broken into smaller pieces, placed in a metal container, and triheptanoin was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 11—Preparation of Acrylated Epoxidized Soybean Oil/Poly(Dimethylsiloxane), bis(3-aminopropyl) Terminated aza-Michael Elastomer with an Acrylate/Primary Amine Functional Group Ratio of 1:1

To a stainless steel or glass reaction vessel was added diisooctyl succinate (209.35 grams) and acrylated epoxidized soybean oil (47.93 grams). The mixture was stirred vigorously for 7 minutes before the addition of DMS A12 (Gelest Inc., 41.79 grams, 1 equivalent of primary amines to acrylate groups). The resultant mixture was stirred vigorously for an additional 3 minutes. 50 grams of the mixture was poured into a 4-ounce glass jar. The remainder of the reaction mixture and the 50-gram sample were covered and heated to 50° C. After 20 hours a transparent rubber had formed. The hardness of the 50-gram sample of rubber was 376 grams force, as determined using a Stable Micro Systems Texture Analyzer with a 5-kilogram load cell fitted with a TA-18B Stable Micro Systems probe and inserted 5 mm into the gel surface.

The aza-Michael elastomeric rubber was broken into smaller pieces, placed in a metal container, and diisooctyl succinate was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 12—Preparation of Acrylated Epoxidized Soybean Oil/Poly(Dimethylsiloxane), bis(3-aminopropyl) Terminated aza-Michael Elastomer with an Acrylate/Primary Amine Functional Group Ratio of 1:0.5

To a stainless steel or glass reaction vessel was added diisooctyl succinate (210.0 grams) and acrylated epoxidized soybean oil (62.67 grams). The mixture was stirred vigorously for 7 minutes before the addition of DMS A12 (Gelest Inc., 27.32 grams, 0.5 equivalent of primary amines to acrylate groups). The resultant mixture was stirred vigorously for an additional 3 minutes. 50 grams of the mixture was poured into a 4-ounce glass jar. The remainder of the reaction mixture and the 50-gram sample were covered and heated to 75° C. After 68 hours a transparent rubber had formed. The hardness of the 50-gram sample of gel was 224 grams force, as determined using a Stable Micro Systems Texture Analyzer with a 5-kilogram load cell fitted with a TA-18B Stable Micro Systems probe and inserted 5 mm into the gel surface.

The aza-Michael elastomeric rubber was broken into smaller pieces, placed in a metal container, and diisooctyl succinate was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 13—Preparation of Acrylated Epoxidized Soybean Oil/Thiocure-332™ thia-Michael Elastomer with an Acrylate/Thiol Functional Group Ratio of 1:1

To a stainless steel or glass reaction vessel was added caprylic/capric triglyceride 324.7 grams) and acrylated epoxidized soybean oil (120.0 grams). The mixture was stirred and Thiocure-332™ (Bruno Bock Thiochemicals, 54.84 grams) was added. After vigorous stirring to produce a homogenous solution, a catalytic quantity of Priamine 1074™ (Croda International Plc, 380 milligrams) was added. The resultant mixture was stirred vigorously for an additional 5 minutes. 50 grams of the mixture was poured into a 4-ounce glass jar. The remainder of the reaction mixture and the 50-gram sample were covered and heated to 80° C. After 22 hours a transparent rubber had formed. The hardness of the 50-gram sample of rubber was 658.5 grams force, as determined using a Stable Micro Systems Texture Analyzer with a 5-kilogram load cell fitted with a TA-18B Stable Micro Systems probe and inserted 5 mm into the gel surface.

The thia-Michael elastomeric rubber was broken into smaller pieces, placed in a metal container, and caprylic/capric triglyceride was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 14—Preparation of a Glyceryl Propoxy Triacrylate/Polymercaptan-358™ thia-Michael Elastomer with an Acrylate/Thiol Functional Group Ratio of 1:1

To a stainless steel or glass reaction vessel was added diisooctyl succinate (217.1 grams) and Polymercaptan-358 (40.0 grams). The mixture was stirred and glyceryl propoxy triacrylate (14.28 grams) was added. After vigorous stirring to produce a homogenous solution, a catalytic quantity of diazabicycloundecene (1080 microliters) was added. The resultant mixture was stirred vigorously for an additional 5 minutes. 50 grams of the mixture was poured into a 4-ounce glass jar. The remainder of the reaction mixture and the 50-gram sample were covered and heated to 80° C. After 22 hours a transparent rubber had formed. The hardness of the 50-gram sample of rubber was 383.6 grams force, as determined using a Stable Micro Systems Texture Analyzer with a 5-kilogram load cell fitted with a TA-18B Stable Micro Systems probe and inserted 5 mm into the gel surface.

The thia-Michael elastomeric rubber was broken into smaller pieces, placed in a metal container, and diisooctyl succinate was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 15—Preparation of Glyceryl Propoxy Triacrylate/Thiocure-333™ thia-Michael Elastomer with an Acrylate/Thiol Functional Group Ratio of 1:1

To a stainless steel or glass reaction vessel was added diisooctyl succinate (55.7 grams) and Thiocure-333™ (Bruno Bock Thiochemicals, 17.9 grams). The mixture was stirred and glyceryl propoxy triacrylate (6.0 grams) was added. After vigorous stirring to produce a homogenous solution, a catalytic quantity of 1-methylimidazole (490 microliters) was added. The resultant mixture was stirred vigorously for an additional 5 minutes. 50 grams of the mixture was poured into a 4-ounce glass jar. The remainder of the reaction mixture and the 50-gram sample were covered and heated to 80° C. After 22 hours a transparent rubber had formed. The hardness of the 50-gram sample of rubber was 435.4 grams force, as determined using a Stable Micro Systems Texture Analyzer with a 5-kilogram load cell fitted with a TA-18B Stable Micro Systems probe and inserted 5 mm into the gel surface.

The thia-Michael elastomeric rubber was broken into smaller pieces, placed in a metal container, and diisooctyl succinate or triheptanoin was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 16—Preparation of Glyceryl Propoxy Triacrylate/Thiocure-1200V Thia-Michael Elastomer with an Acrylate/Thiol Functional Group Ratio of 1:1

To a stainless steel or glass reaction vessel was added diisooctyl succinate (229.3grams) and Thiocure-1200V (Bruno Bock Thiochemicals, 500 grams). The mixture was stirred and glyceryl propoxy triacrylate (26.4 grams) was added. After vigorous stirring to produce a homogenous solution, a catalytic quantity of 1-methylimidazole (490 microliters) was added. The resultant mixture was stirred vigorously for an additional 5 minutes. 50 grams of the mixture was poured into a 4-ounce glass jar. The remainder of the reaction mixture and the 50-gram sample were covered and heated to 80° C. After 22 hours a transparent rubber had formed. The hardness of the 50-gram sample of rubber was 323.5 grams force, as determined using a Stable Micro Systems Texture Analyzer with a 5-kilogram load cell fitted with a TA-18B Stable Micro Systems probe and inserted 5 mm into the gel surface.

The thia-Michael elastomeric rubber was broken into smaller pieces, placed in a metal container, and diisooctyl succinate or triheptanoin was added before homogenizing into a smooth gel paste with a desired viscosity using a Silverson L5M-A homogenizer with a 30 mm diameter rotor, Square Hole High Shear Screen, and operating at 5000 to 10000 revolutions per minute.

Example 17—Preparation of Acrylated Epoxidized Soybean Oil/Priamine 1075® (Croda International, Plc) Elastomer To a stainless steel or glass reaction vessel was added triheptanoin (195.82 grams) and acrylated epoxidized soybean oil (62.36 grams). The mixture was stirred vigorously for 15 minutes, then Priamine® 1075 (Croda International Plc, 43.08 grams, 1 equivalent of amines to acrylate groups) was added and the mixture was stirred for an additional 5 minutes. Once a homogenous mixture was obtained, 50 grams of the mixture was poured into a 4-ounce glass jar. The remainder of the reaction mixture and the 50-gram sample were covered and heated to 80° C. for 24 hours, at which point a translucent rubber was formed. The hardness of the 50-gram sample of gel was 450 grams force, as determined using a Stable Micro Systems Texture Analyzer with a 5-kilogram load cell, fitted with a TA-18B Stable Micro Systems probe, and inserted 5 mm into the gel surface.

The Michael addition elastomer rubber was broken into smaller pieces, placed in a metal container, and triheptanoin was added before homogenizing into a smooth gel paste with a desired viscosity using a Silverson L5M-A homogenizer with a 30 mm diameter rotor, Square Hole High Shear Screen, and operating at 4500 to 8000 revolutions per minute.

Example 18—Preparation of Acrylated Epoxidized Soybean Oil/JEFFAMINE® T-3000 (Huntsman Corporation) Elastomer To a stainless steel or glass reaction vessel was added triheptanoin (240.45 grams) and acrylated epoxidized soybean oil (26.79 grams). The mixture was stirred vigorously for 15 minutes, then JEFFAMINE® T-3000 (Huntsman Corporation, 76.26 grams, 1 equivalent of amines to acrylate groups) was added and the mixture was stirred for an additional 5 minutes. Once a homogenous mixture was obtained, 50 grams of the mixture was poured into a 4-ounce glass jar. The remainder of the reaction mixture and the 50-gram sample were covered and heated to 80° C. for 24 hours, at which point a translucent rubber was formed. The hardness of the 50-gram sample of gel was 324 grams force, as determined using a Stable Micro Systems Texture Analyzer with a 5-kilogram load cell, fitted with a TA-18B Stable Micro Systems probe, and inserted 5 mm into the gel surface.

The Michael addition elastomer rubber was broken into smaller pieces, placed in a metal container, and triheptanoin was added before homogenizing into a smooth gel paste with a desired viscosity using a Silverson L5M-A homogenizer with a 30 mm diameter rotor, Square Hole High Shear Screen, and operating at 4500 to 8000 revolutions per minute.

Example 19—Preparation of Zinc Acrylate/Castor Oil Elastomer

To a test tube add a topically acceptable solvent capable of solubilizing the reactants (37.2 grams) and zinc acrylate (2.97 grams). The mixture can be mixed using an overhead for about 5 minutes at 25° C. to ensure proper mixing. Castor oil (9.61 grams, 1 equivalent of alcohol to acrylate groups) can then be added to the mixture and it can be mixed for an additional 5 minutes at 25° C. to produce a homogenous reaction mixture. No additional catalyst or additives are expected to be required as the zinc is expected to catalyze the reaction mixture. The homogenous mixture can be heated to 80° C. overnight, to form a gel. The hardness of the sample of gel is expected to be about 300 grams force, as determined using a Stable Micro Systems Texture Analyzer with a 5-kilogram load cell, fitted with a TA-18B Stable Micro Systems probe, and inserted 5 mm into the gel surface.

The elastomer gel can be broken into smaller pieces, placed in a container, and subjected to high shear mixing with the simultaneous addition of triheptanoin or another topically acceptable carrier fluid which may or may not be triheptanoin before being sheared into a smooth gel paste with a desired viscosity. Once scaled up to larger quantities the high shear mixing can be accomplished using a Silverson L5M-A homogenizer with a 30 mm diameter rotor, Square Hole High Shear Screen, and operating at 4500 to 8000 revolutions per minute.

Example 20—Preparation of Acrylated Epoxidized Soybean Oil/Pentaerythritol Tetrakis(3-mercaptopropionate) Elastomer To a stainless steel or glass reaction vessel was added heptyl undecylenate (33.02 grams) and acrylated epoxidized soybean oil (12.61 grams). The mixture was stirred for 5 min at 25° C. and pentaerythritol tetrakis(3-mercaptopropionate (4.031 grams, 1 equivalent of thiol to acrylate groups) was added and the mixture was stirred for an additional 5 min. Once homogenous, 1-methylimidazole (0.33 grams) was added and the mixture was stirred for an additional 10 min to ensure proper mixing. The reaction mixture was covered heated to 80° C. for 16 hours, at which point a translucent gel was formed. The hardness of the 50-gram sample of gel is expected to be about 300 grams force, as determined using a Stable Micro Systems Texture Analyzer with a 5-kilogram load cell, fitted with a TA-18B Stable Micro Systems probe, and inserted 5 mm into the gel surface.

To produce a gel paste, the gel can be broken into smaller pieces, placed in a metal container, and a topically acceptable carrier fluid, which may or may not be triheptanoin, can be added before the mixture is homogenized into a smooth gel paste with a desired viscosity using a Silverson L5M-A homogenizer with a 30 mm diameter rotor, Square Hole High Shear Screen, and operating at 4500 to 8000 revolutions per minute.

Example 21—Preparation of Acrylated Epoxidized Soybean Oil/2,2'-(ethylenedioxane) diethanethiol elastomer To a stainless steel or glass reaction vessel was added heptyl undecylenate (37.45 grams) and acrylated epoxidized soybean oil (9.94 grams). The mixture was stirred for 5 min at 25° C. and 2,2'-(Ethylenedioxane) diethanethiol (2.35 grams, 1 equivalent of thiol to acrylate groups) was added and the mixture was stirred for an additional 5 min. Once homogenous, Priamine 1075 (Croda; 0.35 grams) was added and the mixture was stirred for an additional 10 min to ensure proper mixing. The reaction mixture was covered and heated to 80° C. overnight, at which point a translucent gel was formed. The hardness of the 50-gram sample of gel is expected to be about 300 grams force, as determined using a Stable Micro Systems Texture Analyzer with a 5-kilogram load cell, fitted with a TA-18B Stable Micro Systems probe, and inserted 5 mm into the gel surface.

To produce a gel paste, the gel can be broken into smaller pieces, placed in a metal container, and a topically acceptable carrier fluid, which may or may not be triheptanoin, can be added before the mixture is homogenized into a smooth gel paste with a desired viscosity using a Silverson L5M-A homogenizer with a 30 mm diameter rotor, Square Hole High Shear Screen, and operating at 4500 to 8000 revolutions per minute.

Example 22—Fourier-Transform Infrared Spectroscopy of Polyurethane Elastomers Fourier-Transform Infrared Spectroscopy (FTIR) was performed to analyze the molecular structures of the polyurethane elastomers.

Figure 1:
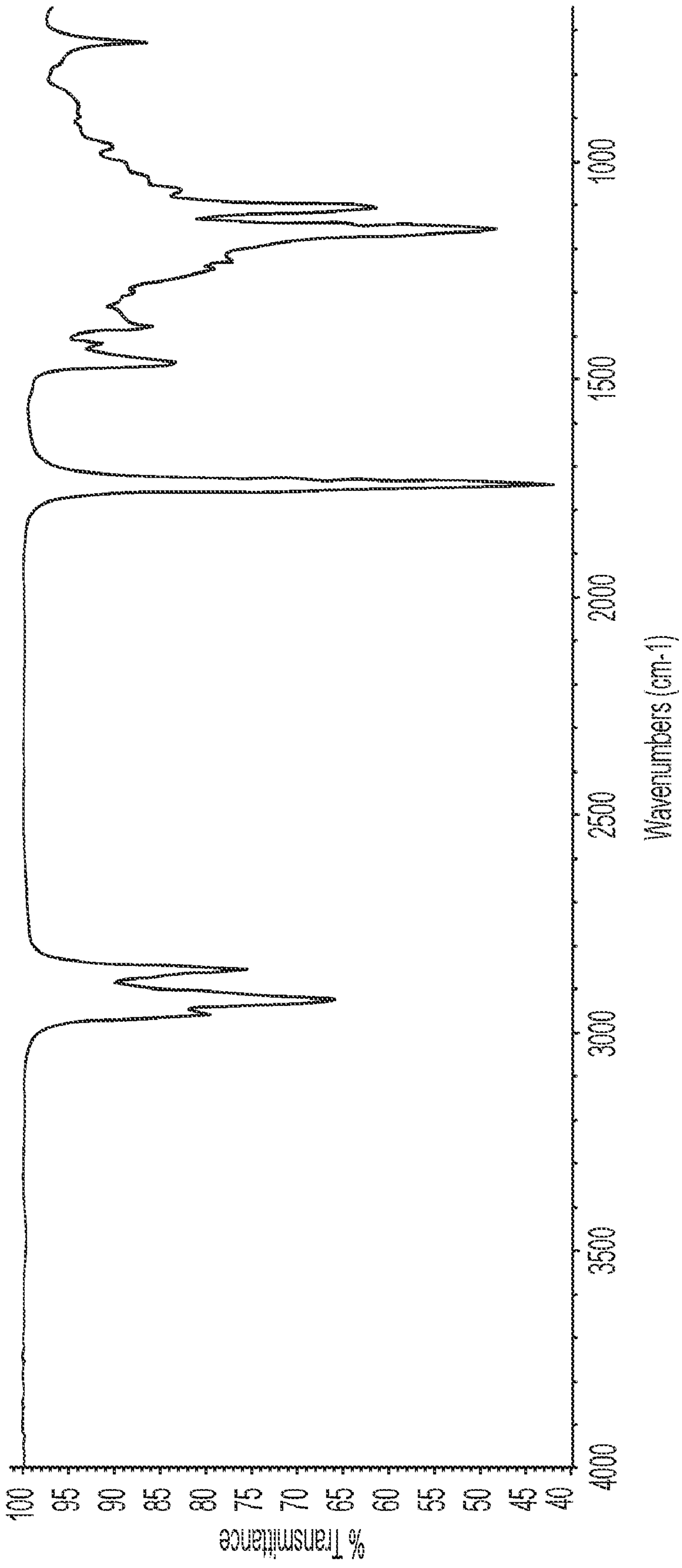
FIG. 1 shows an exemplary FTIR spectrograph of propoxylate triacrylate/Priamine™ 1075 aza-Michael elastomer with an acrylate/primary amine functional group ratio of 1:1, as described in embodiments herein.

The FTIR spectrograph of propoxylate triacrylate/Priamine™ 1075 aza-Michael elastomer with an acrylate/primary amine functional group ratio of 1:1 is shown in FIG. 1.

Figure 2:
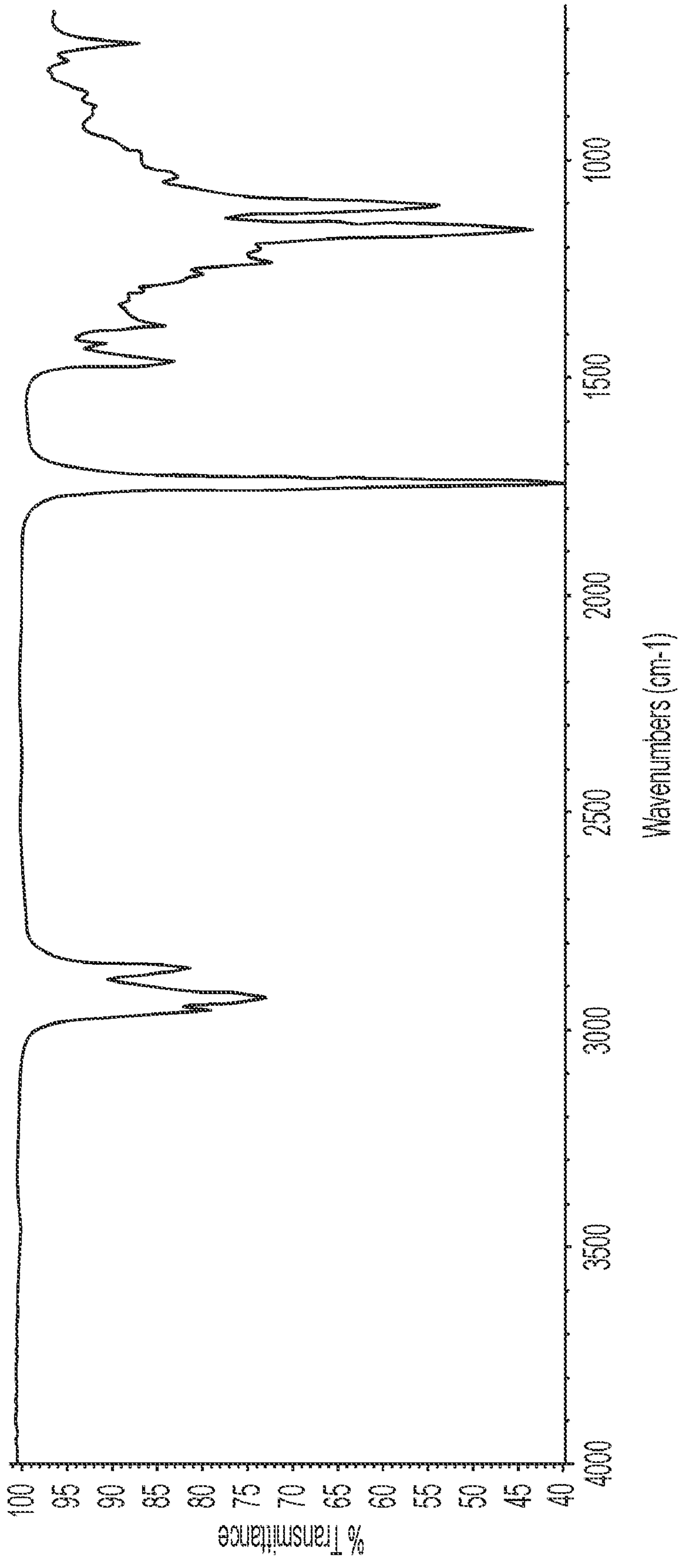
FIG. 2 shows an exemplary FTIR spectrograph of glycerol propoxylate triacrylate/Priamine™ 1075 aza-Michael elastomer with an acrylate/primary amine functional group ratio of 1:0.5, as described in embodiments herein.

The FTIR spectrograph of glycerol propoxylate triacrylate/Priamine™ 1075 aza-Michael elastomer with an acrylate/primary amine functional group ratio of 1:0.5 is shown in FIG. 2.

The FTIR spectrograph of glycerol propoxylate triacrylate/Priamine™ 1075 aza-Michael elastomer with an acrylate/primary amine functional group ratio of 1:0.5 is shown in FIG. 2.

Figure 3:
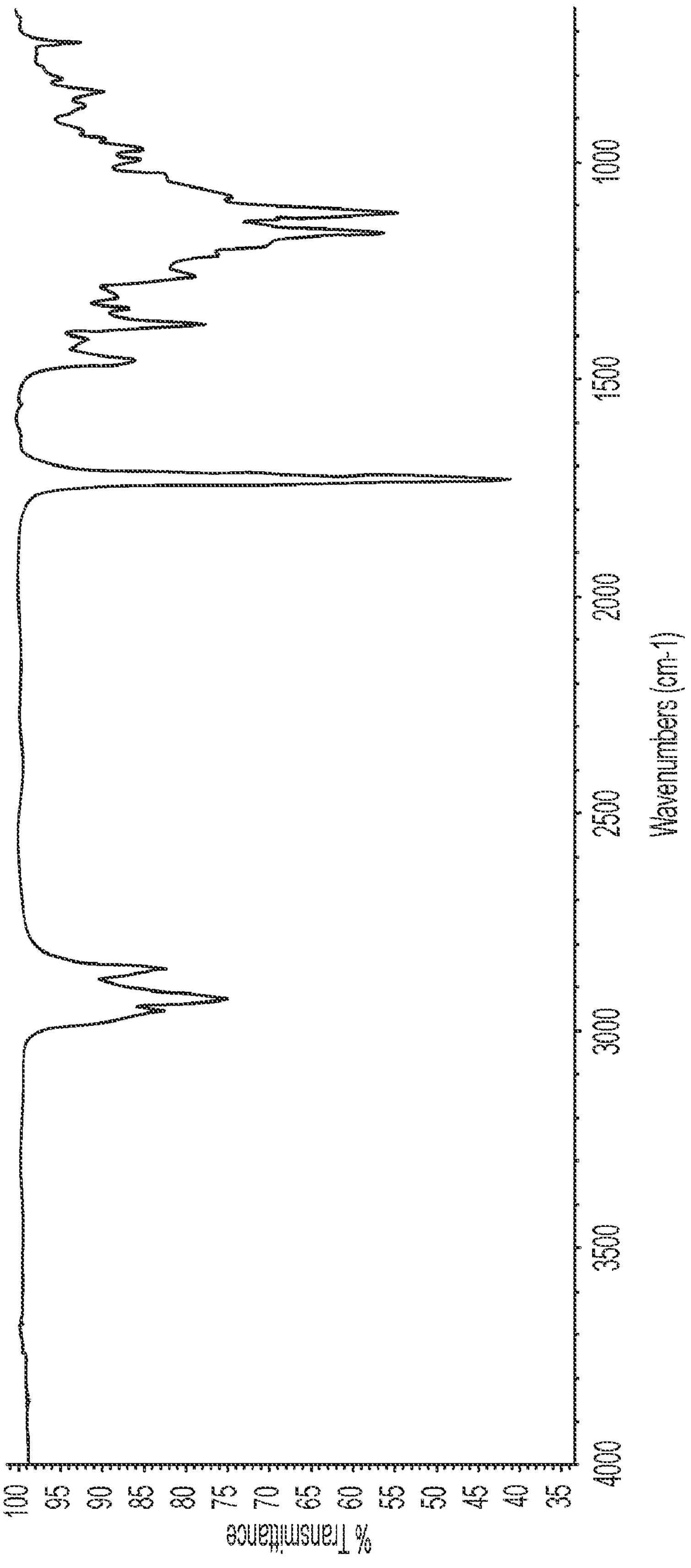
FIG. 3 shows an exemplary FTIR spectrograph of glycerol propoxylate triacrylate/JEFFAMINE® T-403 aza-Michael elastomer with an acrylate/primary amine functional group ratio of 1:1, as described in embodiments herein.

The FTIR spectrograph of glycerol propoxylate triacrylate/JEFFAMINE® T-403 aza-Michael elastomer with an acrylate/primary amine functional group ratio of 1:1 is shown in FIG. 3.

Figure 4:
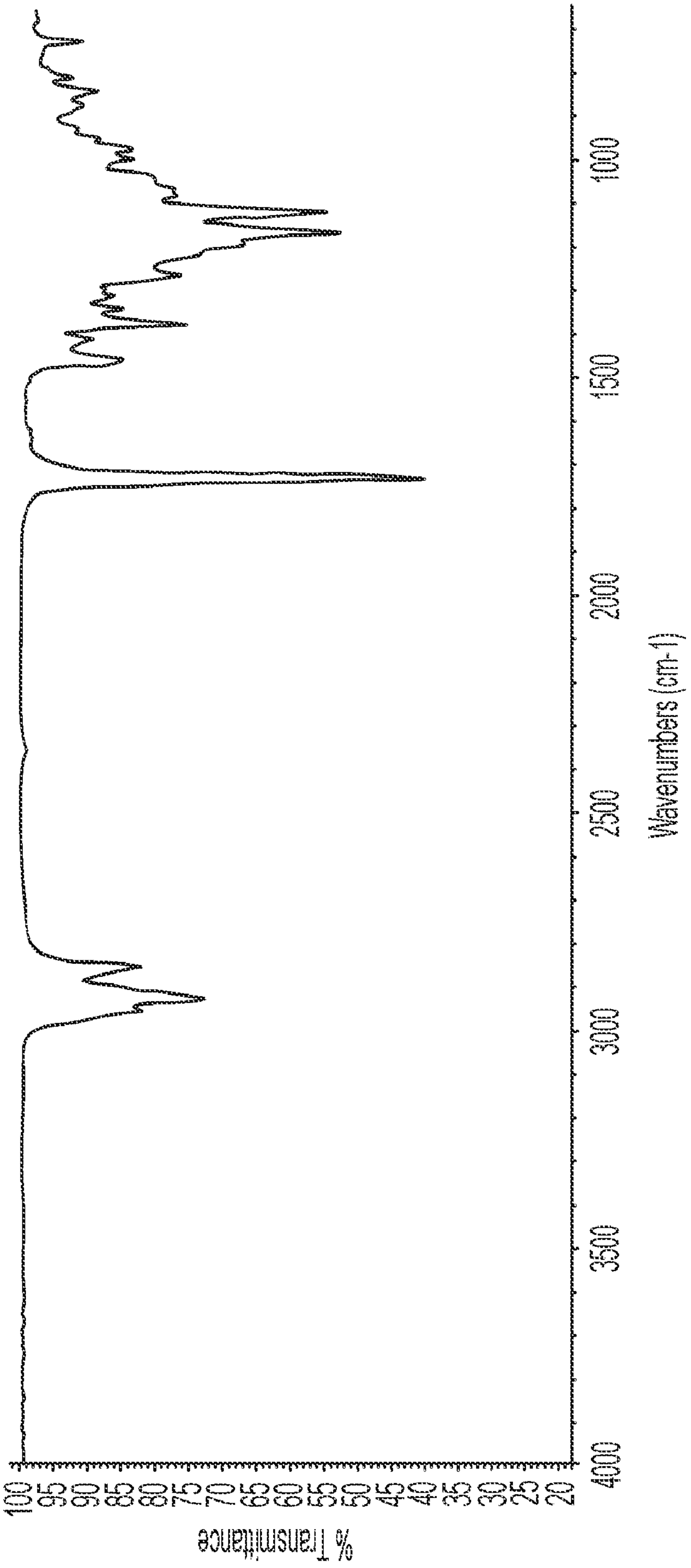
FIG. 4 shows an exemplary FTIR spectrograph of glycerol propoxylate triacrylate/JEFFAMINE® T-403 aza-Michael elastomer with an acrylate/primary amine functional group ratio of 1:0.5, as described in embodiments herein.

The FTIR spectrograph of glycerol propoxylate triacrylate/JEFFAMINE® T-403 aza-Michael elastomer with an acrylate/primary amine functional group ratio of 1:0.5 is shown in FIG. 4.

Figure 5:
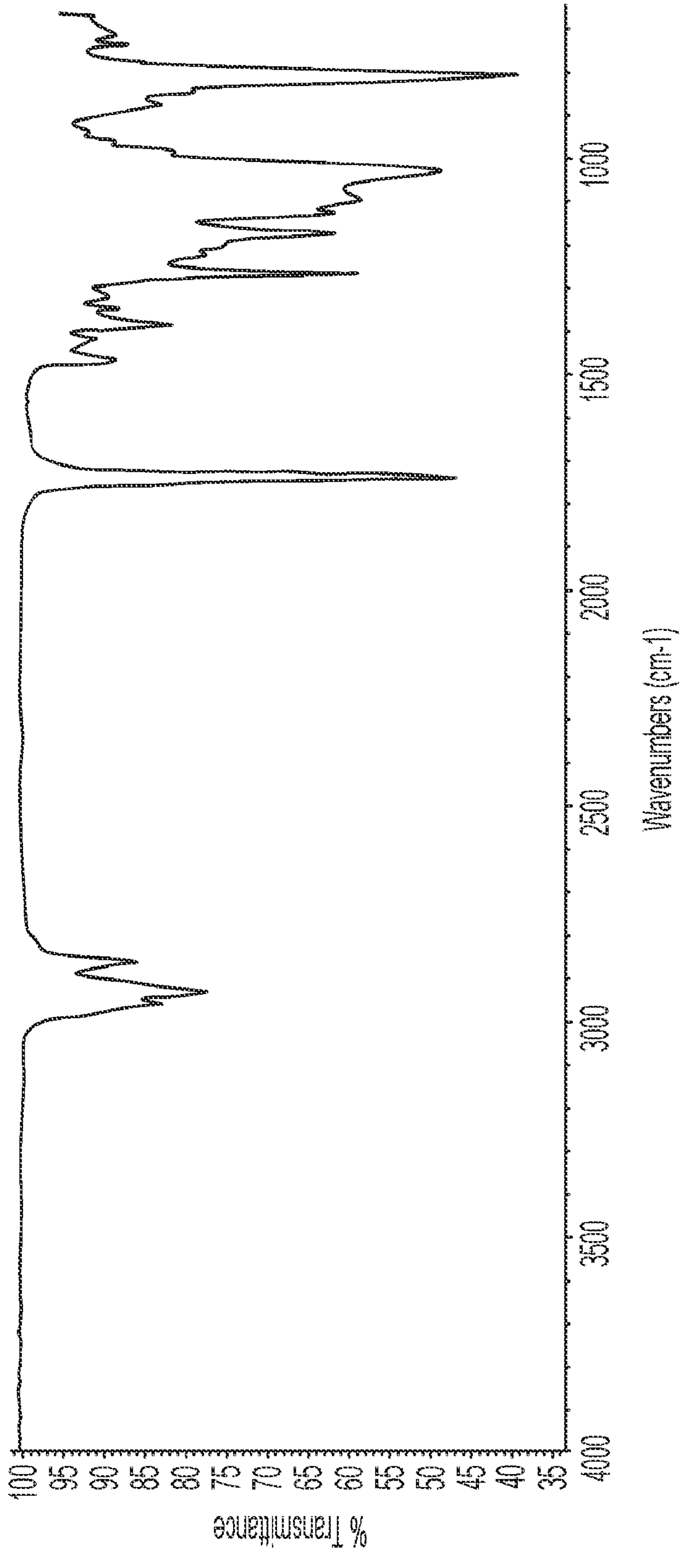
FIG. 5 shows an exemplary FTIR spectrograph glycerol Propoxylate triacrylate/poly(dimethylsiloxane), bis(3-aminopropyl) terminated aza-Michael elastomer with an acrylate/primary amine functional group ratio of 1:1, as described in embodiments herein.

The FTIR spectrograph glycerol propoxylate triacrylate/poly(dimethylsiloxane), bis(3-aminopropyl) terminated aza-Michael elastomer with an acrylate/primary amine functional group ratio of 1:1 is shown in FIG. 5.

Figure 6:
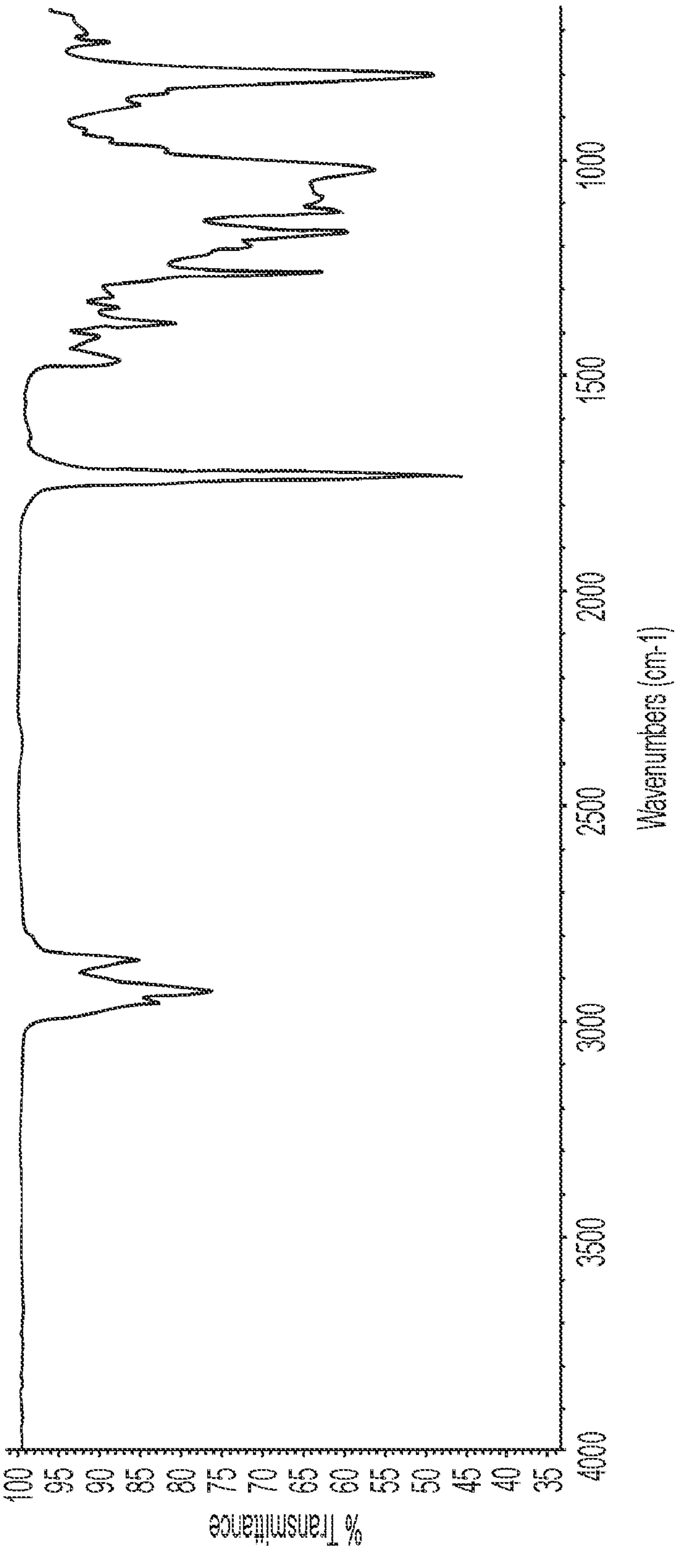
FIG. 6 shows an exemplary FTIR spectrograph glycerol Propoxylate triacrylate/poly(dimethylsiloxane), bis(3-aminopropyl) terminated aza-Michael elastomer with an acrylate/primary amine functional group ratio of 1:0.5, as described in embodiments herein.

The FTIR spectrograph glycerol propoxylate triacrylate/poly(dimethylsiloxane), bis(3-aminopropyl) terminated aza-Michael elastomer with an acrylate/primary amine functional group ratio of 1:0.5 is shown in FIG. 6.

Figure 7:
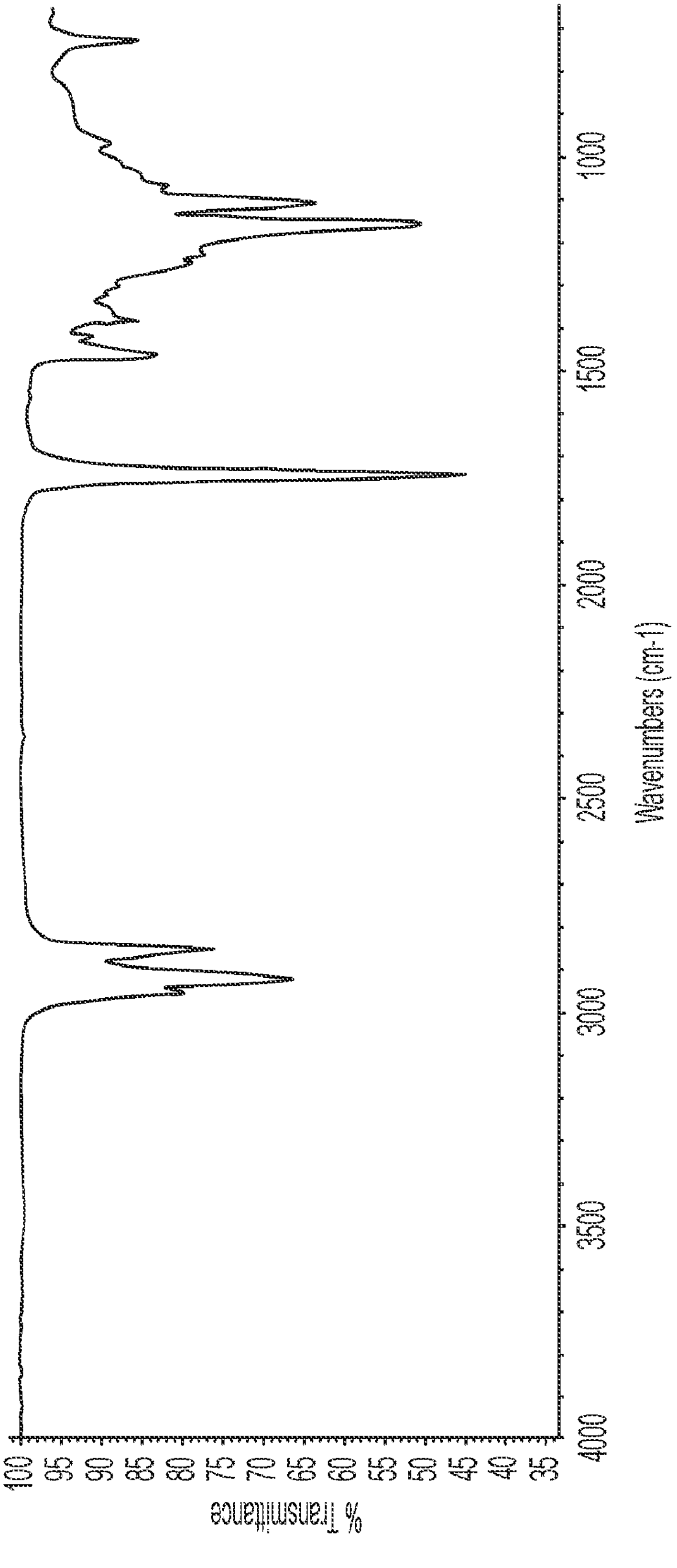
FIG. 7 shows an exemplary FTIR spectrograph acrylated epoxidized soybean oil/Priamine™ 1074 aza-Michael elastomer with an acrylate/primary amine functional group ratio of 1:1, as described in embodiments herein.

The FTIR spectrograph acrylated epoxidized soybean oil/Priamine™ 1074 aza-Michael elastomer with an acrylate/primary amine functional group ratio of 1:1 is shown in FIG. 7.

Figure 8:
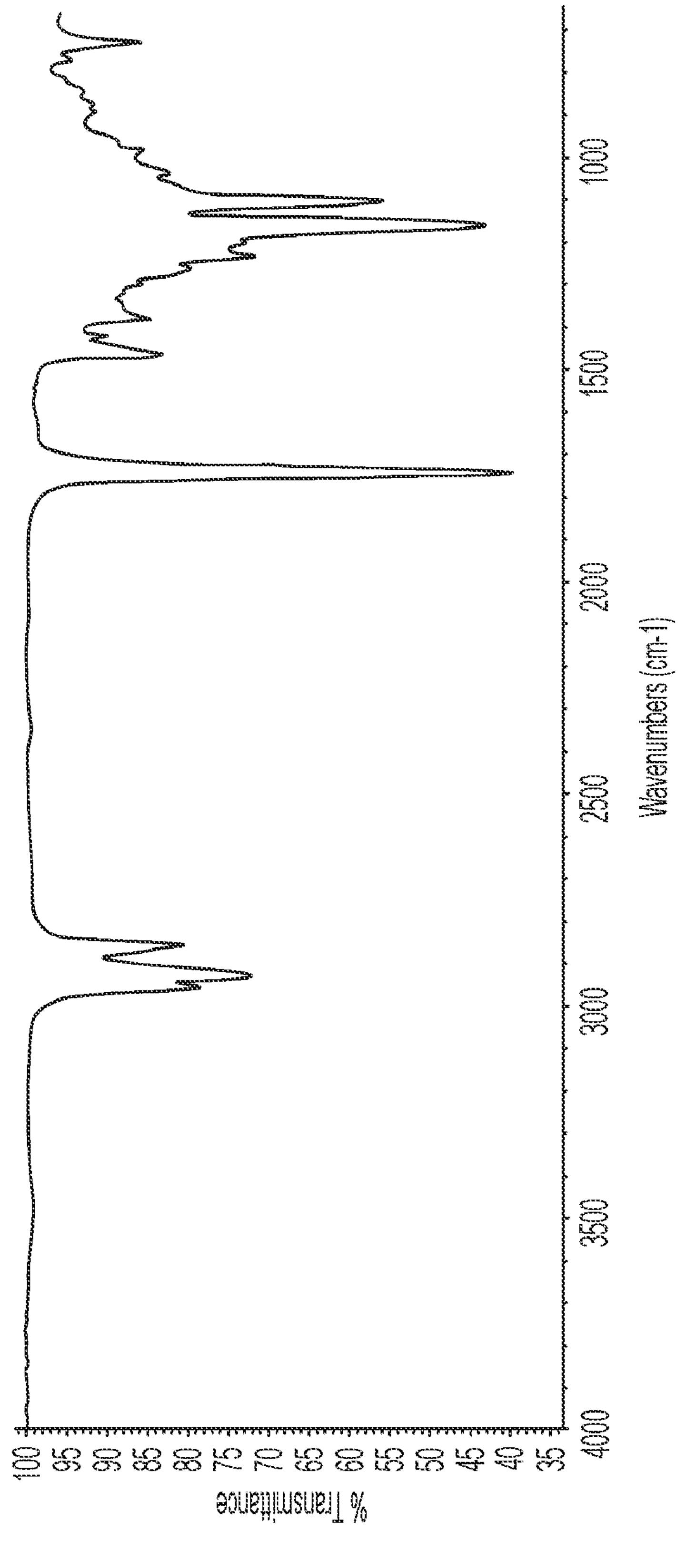
FIG. 8 shows an exemplary FTIR spectrograph acrylated epoxidized soybean oil/Priamine™ 1074 aza-Michael elastomer with an acrylate/primary amine functional group ratio of 1:0.5, as described in embodiments herein.

The FTIR spectrograph acrylated epoxidized soybean oil/Priamine™ 1074 aza-Michael elastomer with an acrylate/primary amine functional group ratio of 1:0.5 is shown in FIG. 8.

Figure 9:
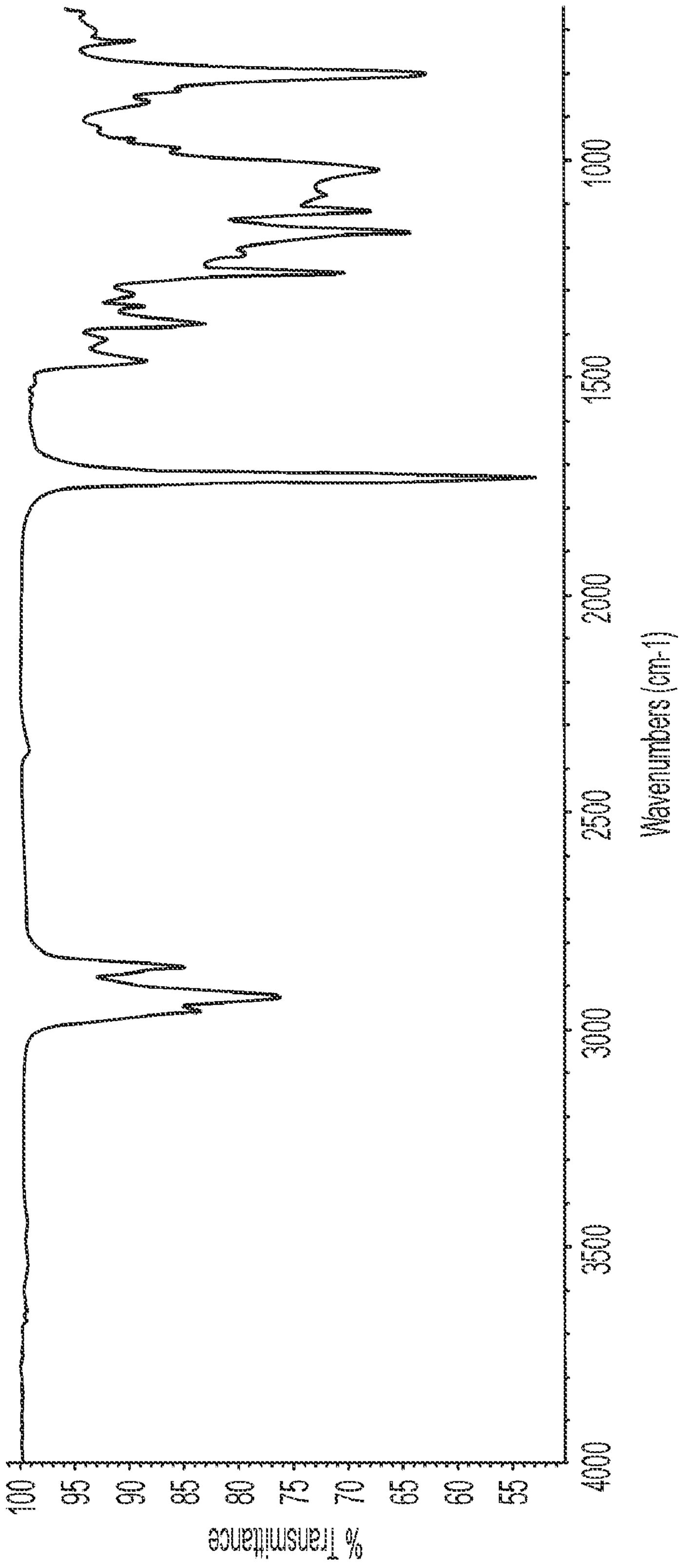
FIG. 9 shows an exemplary FTIR spectrograph of acrylated epoxidized soybean oil/poly(dimethylsiloxane), bis(3-aminopropyl) terminated aza-Michael elastomer with an acrylate/primary amine functional group ratio of 1:1, as described in embodiments herein.

The FTIR spectrograph of acrylated epoxidized soybean oil/poly(dimethylsiloxane), bis(3-aminopropyl) terminated aza-Michael elastomer with an acrylate/primary amine functional group ratio of 1:1 is shown in FIG. 9.

The FTIR spectrograph of acrylated epoxidized soybean oil/poly(dimethylsiloxane), bis(3-aminopropyl) terminated aza-Michael elastomer with an acrylate/primary amine functional group ratio of 1:0.5 is shown in FIG. 10.

The invention claimed is:

1. A gel composition comprising a Michael addition elastomer being the reaction product of:

a) a first reactant comprising one or more molecules, wherein each of the one or more molecules comprises two or more Michael acceptor functional groups, optionally wherein the two or more Michael acceptor functional groups are coordinated by zinc, and optionally wherein the first reactant comprises an OH, SH or NH functional group at a vicinal position to each of the Michael acceptor functional groups;

b) a second reactant comprising one or more molecules, wherein each of the one or more molecules comprises a Michael donor functional group capable of reacting with the two or more Michael acceptor functional groups to form 1,4-addition products, wherein the Michael donor functional group comprises a primary or secondary amine, a thiol, a hydroxyl group, or a carbon bonded to two Michael donor hydrogen atoms;

c) an optional reaction catalyst; and d) a topically acceptable carrier fluid, at a concentration of 60% (w/w) to 99.9% (w/w) of the gel composition, wherein the topically acceptable carrier fluid is selected from the group consisting of esters, triglycerides, hydrocarbons, silicone fluids, and combinations thereof, and the topically acceptable carrier fluid is acceptable for cutaneous surfaces.

2. The gel composition of claim 1, wherein the topically acceptable carrier fluid is selected from the group consisting of triheptanoin, diisooctyl succinate, caprylic/capric triglyceride, heptyl undecylenate, neopentyl glycol diheptanoate, coco-caprylate/caprate, diisopropyl adipate, isoamyl laurate, isopropyl myristate, jojoba esters, methylheptyl Isostearate, neopentyl glycol diheptanoate, dicaprylin caprylic/capric/myristic/stearic triglyceride, caprylic/capric/succinic triglyceride, ethyl hexyl olivate, C15-C16 branched alkanes, C17-C18 branched alkanes, dodecane, hexadecane, squalene, hemisqualane, tetradecane, undecane, tridecane, coconut alkanes, C9-12 alkane, and combinations thereof.

3. The gel composition of claim 1, further comprising a pharmaceutically active ingredient, wherein the pharmaceutically active ingredient is dissolved in the topically acceptable carrier fluid or incorporated in the gel.

4. The gel composition of claim 1, wherein:

the first reactant comprises acrylated epoxidized soybean oil or glycerol propoxylate triacrylate, the second reactant is selected from PRIPLAST™ 1075, PRIAMINE™ 1074, JEFFAMINE® T-403, JEFFAMINE® T-3000, and poly(dimethylsiloxane), bis(3-aminopropyl) terminated, wherein the ratio of primary amines to acrylate groups is about 0.25 to 2, and the carrier fluid is triheptanoin, diisooctyl succinate, or caprylic/capric triglyceride;

the first reactant comprises acrylated epoxidized soybean oil, the second reactant is Thiocure-332™, wherein the ratio of thiols to acrylate groups is about 0.25 to 2, and the carrier fluid is triheptanoin, diisooctyl succinate, or caprylic/capric triglyceride;

the first reactant comprises glycerol propoxylate triacrylate, the second reactant is selected from Polymercaptan-358™, Thiocure-333™, and Thiocure-1200V™, wherein the ratio of thiols to acrylate groups is about 0.25 to 2 equivalents, and the carrier fluid is triheptanoin, diisooctyl succinate, or caprylic/capric triglyceride; or the first reactant is zinc acrylate.

5. The gel composition of claim 1, wherein the first reactant is prepared from a vegetable oil or mixture thereof, wherein the vegetable oil comprises two or more hydroxyl groups or epoxides; or wherein the first reactant is prepared with two or more Michael acceptor functional groups from linseed oil, soybean oil, or other vegetable oils.

6. A Michael addition elastomer gel paste made by:

i) shearing the Michael addition elastomer in the gel composition of claim 1;

ii) optionally adding additional quantities of the topically acceptable carrier fluid during shearing to produce a gel paste composition; and iii) optionally adding a pharmaceutically active ingredient.

7. A topical formulation comprising:

the gel composition of claim 3, wherein the pharmaceutically active ingredient is a personal care active ingredient or a healthcare active ingredient.

8. A topical formulation comprising:

the Michael addition elastomer gel paste of claim 6, comprising a personal care active ingredient or a healthcare active ingredient.

9. A gel composition comprising:

a) a first reactant comprising one or more molecules, wherein each of the one or more molecules comprises two or more Michael acceptor functional groups;

b) a second reactant comprising one or more molecules, wherein each of the one or more molecules comprises a Michael donor functional group capable of reacting with a Michael acceptor group to form 1,4-addition products, wherein the Michael donor functional group comprises a primary amine or a carbon bonded to two Michael donor hydrogen atoms;

c) an optional reaction catalyst; and d) a topically acceptable carrier fluid, at a concentration of between 60% (w/w) and 99.9% (w/w) of the gel composition, wherein the topically acceptable carrier fluid is selected from the group consisting of esters, triglycerides, hydrocarbons, silicone fluids, and combinations thereof, and the topically acceptable carrier fluid is acceptable for cutaneous surfaces.

10. A foot conforming shoe insert or shoe sole comprising:

the gel composition comprising of claim 1.

11. A medically acceptable gel comprising:

the gel composition comprising of claim 1.

12. A topical formulation comprising:

the gel composition comprising of claim 1.

13. A method of making a Michael addition elastomer gel paste comprising the steps of:

i) shearing the gel composition of claim 1;

ii) optionally adding quantities of the topically acceptable carrier fluid during shearing to produce a gel paste composition; and iii) optionally adding a pharmaceutically active ingredient.

14. A Michael addition elastomer gel paste prepared by the method of claim 13.

15. A topical formulation comprising the Michael addition elastomer gel paste of claim 14.

16. A gel composition comprising a Michael addition elastomer being the reaction product of:

a) a first reactant comprising one or more molecules, wherein each of the one or more molecules comprises two or more Michael acceptor functional groups;

b) a second reactant comprising one or more molecules, wherein each of the one or more molecules comprises a Michael donor functional group, wherein the Michael donor functional group comprises two or more Michael active hydrogen atoms;

c) an optional reaction catalyst; and d) a topically acceptable carrier fluid, at a concentration of 60% (w/w) to 99.9% (w/w) of the gel composition, wherein the topically acceptable carrier fluid is selected from the group consisting of esters, triglycerides, hydrocarbons, silicone fluids, and combinations thereof, and the topically acceptable carrier fluid is acceptable for cutaneous surfaces.

17. The gel composition of claim 1, wherein a mixture reaction comprising a), b), and optionally c) is heated to about 50° C. to 120° C. to form the Michael addition elastomer.

* * * * *